US009850281B2

(12) United States Patent
Hafner et al.

(10) Patent No.: US 9,850,281 B2
(45) Date of Patent: Dec. 26, 2017

(54) CLADOSPORIUM PEPTIDES

(71) Applicant: Circassia Limited, Oxford (GB)

(72) Inventors: Roderick Peter Hafner, Oxford (GB); Paul Laidler, Oxford (GB); Pascal Hickey, Oxford (GB); Mark Larche, Ontario (CA)

(73) Assignee: Circassia Limited, Oxford (GB)

( * ) Notice: Subject to any disclaimer, the term of this patent is extended or adjusted under 35 U.S.C. 154(b) by 62 days.

(21) Appl. No.: 14/403,462

(22) PCT Filed: May 30, 2013

(86) PCT No.: PCT/GB2013/051440
§ 371 (c)(1),
(2) Date: Nov. 24, 2014

(87) PCT Pub. No.: WO2013/179044
PCT Pub. Date: Dec. 5, 2013

(65) Prior Publication Data
US 2015/0218215 A1 Aug. 6, 2015

(30) Foreign Application Priority Data
Jun. 1, 2012 (GB) .................................. 1209862.0

(51) Int. Cl.
*A61K 38/00* (2006.01)
*C07K 7/08* (2006.01)
*A61K 39/35* (2006.01)
*C07K 14/37* (2006.01)
*G01N 33/50* (2006.01)

(52) U.S. Cl.
CPC ................ *C07K 7/08* (2013.01); *A61K 39/35* (2013.01); *C07K 14/37* (2013.01); *G01N 33/505* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 2005/0124055 A1 | 6/2005 | Simon-Nobbe et al. | |
| 2011/0206709 A1 | 8/2011 | Larche et al. | |
| 2012/0014978 A1 | 1/2012 | Hafner et al. | |

FOREIGN PATENT DOCUMENTS

| | | | |
|---|---|---|---|
| CA | 2204362 A1 | | 5/1996 |
| CA | 2217173 A1 | | 5/1999 |
| CN | 101178406 A | | 5/2008 |
| CN | 101387643 A | | 3/2009 |
| CN | 101393215 A | | 3/2009 |
| CN | 102212531 A | | 10/2011 |
| WO | 96/14407 A1 | | 5/1996 |
| WO | 96/27005 A2 | | 9/1996 |
| WO | 2009/022154 A2 | | 2/2009 |
| WO | 2010/061193 A2 | | 6/2010 |
| WO | 2011/098778 A2 | | 8/2011 |
| WO | 2012/049310 A1 | | 4/2012 |
| WO | WO 2013/119853 | * | 8/2013 |

OTHER PUBLICATIONS

Franco et al (ABO76721, 2007).*
NCBI XP_007928837.1 (downloaded online on Sep. 11, 2015 from URL:<http://www.ncbi.nlm.nih.gov/protein/631388914?report=genbank&log$=protalign&blast_rank=4&RID=Z58HMZ08014>).*
U.S. Appl. No. 13/131,505, filed Oct. 5, 2011, Roderick Peter Hafner.
U.S. Appl. No. 14/403,464, filed Nov. 24, 2014, Roderick Peter Hafner.
U.S. Appl. No. 13/131,505, Office Action Dated Jan. 13, 2015.
U.S. Appl. No. 13/131,505, Office Action Dated Sep. 26, 2014.
U.S. Appl. No. 13/131,505, Office Action Dated Apr. 25, 2014.
U.S. Appl. No. 13/131,505, Office Action Dated Sep. 10, 2013.
U.S. Appl. No. 13/131,505, Office Action Dated Mar. 14, 2013.
Chou et al., 2008, International Archives of Allergy and Immunology, 146(4): 277-286.
Kurup et al., 2003, Peptides, 24(2): 179-185.
Montalbano et al., 2003, J Allergy Clin Immunol, 111(2): S88 Abstract.
Sanchez et al., 1997, J Allergy Clin Immunol,99(1): S391, 1594 Abstract.
Simon-Nobbe et al., 2000, J Allergy Clin Immunol, 106: 887-895.
Yi, H-Q, et al., "Isolation, identification and partial purification of specific allergens from Aspergillus versicolor," Chinese Journal of Public Health, vol. 27(5): 661-662 (2011).

* cited by examiner

*Primary Examiner* — James H Alstrum Acevedo
*Assistant Examiner* — Sergio Coffa
(74) *Attorney, Agent, or Firm* — Nelson Mullins Riley & Scarborough LLP; Jane E. Remillard, Esq.; Jeanne M. DiGiorgio, Esq.

(57) ABSTRACT

Polypeptides which may be used for preventing or treating allergy to moulds of the *Cladosporium* and/or *Alternaria* genus, have up to 30 amino acids in length and comprise: (I) the amino acid sequence: (a) GGYKAAVRPTMLE (SEQ ID NO: 35; Cla35), (b) AE V YQKLK SLTKK (SEQ ID NO: 31; Cla16), (c) VAITYASRAQGAE (SEQ ID NO: 32; Cla25), (d) GHHFKERGT-GSLVIT (SEQ ID NO: 33; Cla26), or (e) ANYTQTKTVSIRL (SEQ ID NO: 34; Cla29); or (II) a T cell epitope-containing variant sequence which is a said amino acid sequence (I) having up to six amino acid modifications, each of which is independently a deletion, substitution or insertion.

28 Claims, No Drawings

SEQUENCE LISTING

<160> NUMBER OF SEQ ID NOS: 57

<210> SEQ ID NO 1
<211> LENGTH: 18
<212> TYPE: PRT
<213> ORGANISM: Artificial Sequence
<220> FEATURE:
<223> OTHER INFORMATION: synthetic peptide

<400> SEQUENCE: 1

Ala Glu Val Tyr Gln Lys Leu Lys Ser Leu Thr Lys Lys Arg Tyr Gly
1 5 10 15

Gln Ser

<210> SEQ ID NO 2
<211> LENGTH: 21
<212> TYPE: PRT
<213> ORGANISM: Artificial Sequence
<220> FEATURE:
<223> OTHER INFORMATION: synthetic peptide

<400> SEQUENCE: 2

Glu Ala Gly Tyr Thr Gly Gln Ile Lys Ile Ala Met Asp Val Ala Ser
1 5 10 15

Ser Glu Phe Tyr Lys
20

<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

Lys Asp Ser Phe Ala Ala Gly Trp Gly Val Met Val Ser His Arg Ser
1 5 10 15

Gly Glu Thr Glu Asp Val
20

<210> SEQ ID NO 4
<211> LENGTH: 16
<212> TYPE: PRT
<213> ORGANISM: Artificial Sequence
<220> FEATURE:
<223> OTHER INFORMATION: synthetic peptide

<400> SEQUENCE: 4

Ile Ala Asp Ile Val Val Gly Leu Arg Ala Gly Gln Ile Lys Thr Gly
1 5 10 15

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Met Ala Val Ala Lys Ala Ala Ala Ala
1 5

<210> SEQ ID NO 6
<211> LENGTH: 9
<212> TYPE: PRT

<213> ORGANISM: Artificial Sequence
<220> FEATURE:
<223> OTHER INFORMATION: synthetic peptide

<400> SEQUENCE: 6

Tyr Gln Lys Leu Lys Ser Leu Thr Lys
1 5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Trp Gly Val Met Val Ser His Arg Ser
1 5

<210> SEQ ID NO 8
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Tyr Thr Gly Gln Ile Lys Ile Ala Met
1 5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Ile Lys Ile Ala Met Asp Val Ala Ser
1 5

<210> SEQ ID NO 10
<211> LENGTH: 23
<212> TYPE: PRT
<213> ORGANISM: Artificial Sequence
<220> FEATURE:
<223> OTHER INFORMATION: synthetic peptide

<400> SEQUENCE: 10

Cys Ala Glu Met Gly Ala Ala Val Ala Ile Thr Tyr Ala Ser Arg Ala
1 5 10 15

Gln Gly Ala Glu Glu Asn Val
20

<210> SEQ ID NO 11
<211> LENGTH: 25
<212> TYPE: PRT
<213> ORGANISM: Artificial Sequence
<220> FEATURE:
<223> OTHER INFORMATION: synthetic peptide

<400> SEQUENCE: 11

Gly His His Phe Lys Glu Arg Gly Thr Gly Ser Leu Val Ile Thr Ala
1 5 10 15

Ser Met Ser Gly His Ile Ala Asn Phe
20 25

<210> SEQ ID NO 12
<211> LENGTH: 22
<212> TYPE: PRT
<213> ORGANISM: Artificial Sequence
<220> FEATURE:
<223> OTHER INFORMATION: synthetic peptide

<400> SEQUENCE: 12

```
Ala Lys Glu Leu Lys Gly Ala Tyr Val Tyr Phe Ala Ser Asp Ala Ser
1               5                   10                  15

Thr Tyr Thr Thr Gly Ala
            20
```

<210> SEQ ID NO 13
<211> LENGTH: 9
<212> TYPE: PRT
<213> ORGANISM: Artificial Sequence
<220> FEATURE:
<223> OTHER INFORMATION: synthetic peptide

<400> SEQUENCE: 13

```
Ile Thr Tyr Ala Ser Arg Ala Gln Gly
1               5
```

<210> SEQ ID NO 14
<211> LENGTH: 9
<212> TYPE: PRT
<213> ORGANISM: Artificial Sequence
<220> FEATURE:
<223> OTHER INFORMATION: synthetic peptide

<400> SEQUENCE: 14

```
Glu Arg Gly Thr Gly Ser Leu Val Ile
1               5
```

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

```
Tyr Asn Val Ala Lys Ala Gly Cys Ile
1               5
```

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

```
Trp Arg Asp Phe Ala Arg Val Asn Ser
1               5
```

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

-continued

Phe Val Pro Lys Glu Thr Gln Gln Leu
1 5

<210> SEQ ID NO 18
<211> LENGTH: 9
<212> TYPE: PRT
<213> ORGANISM: Artificial Sequence
<220> FEATURE:
<223> OTHER INFORMATION: synthetic peptide

<400> SEQUENCE: 18

Trp His Ser Met Ile Pro Met Gly Arg
1 5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Leu Lys Gly Ala Tyr Val Tyr Phe Ala
1 5

<210> SEQ ID NO 20
<211> LENGTH: 9
<212> TYPE: PRT
<213> ORGANISM: Artificial Sequence
<220> FEATURE:
<223> OTHER INFORMATION: synthetic peptide

<400> SEQUENCE: 20

Tyr Val Tyr Phe Ala Ser Asp Ala Ser
1 5

<210> SEQ ID NO 21
<211> LENGTH: 19
<212> TYPE: PRT
<213> ORGANISM: Artificial Sequence
<220> FEATURE:
<223> OTHER INFORMATION: synthetic peptide

<400> SEQUENCE: 21

Arg Gln Ala Phe Glu Gly Ser Trp Arg Leu Glu Thr Pro Glu Asn Arg
1 5 10 15

Gly Lys Leu

<210> SEQ ID NO 22
<211> LENGTH: 17
<212> TYPE: PRT
<213> ORGANISM: Artificial Sequence
<220> FEATURE:
<223> OTHER INFORMATION: synthetic peptide

<400> SEQUENCE: 22

Pro Asp Thr Phe Asn Tyr Val Lys Lys Glu Pro Ile Gly Val Cys Arg
1 5 10 15

Ser

<210> SEQ ID NO 23
<211> LENGTH: 21
<212> TYPE: PRT
<213> ORGANISM: Artificial Sequence
<220> FEATURE:
<223> OTHER INFORMATION: synthetic peptide

<400> SEQUENCE: 23

Gly Ser Thr Val Val Gly Arg Thr Ile Leu Lys Ala Ala Ala Ser Ser
1 5 10 15

Asn Leu Lys Lys Val
20

<210> SEQ ID NO 24
<211> LENGTH: 20
<212> TYPE: PRT
<213> ORGANISM: Artificial Sequence
<220> FEATURE:
<223> OTHER INFORMATION: synthetic peptide

<400> SEQUENCE: 24

Ala Ile Ser Trp Val Asn Phe Gly Ile Phe Phe Asn His Gly Gln Cys
1 5 10 15

Cys Cys Ala Gly
20

<210> SEQ ID NO 25
<211> LENGTH: 21
<212> TYPE: PRT
<213> ORGANISM: Artificial Sequence
<220> FEATURE:
<223> OTHER INFORMATION: synthetic peptide

<400> SEQUENCE: 25

Tyr Asp Lys Phe Val Gln Lys Phe Lys Glu Arg Ala Gln Lys Asn Val
1 5 10 15

Val Gly Asp Pro Phe
20

<210> SEQ ID NO 26
<211> LENGTH: 23
<212> TYPE: PRT
<213> ORGANISM: Artificial Sequence
<220> FEATURE:
<223> OTHER INFORMATION: synthetic peptide

<400> SEQUENCE: 26

Glu Asp Ala Ile Lys Leu Gly Asn Ala Ser Thr Tyr Gly Leu Ala Ala
1 5 10 15

Ala Val His Thr Lys Asn Leu
20

<210> SEQ ID NO 27
<211> LENGTH: 20
<212> TYPE: PRT
<213> ORGANISM: Artificial Sequence
<220> FEATURE:
<223> OTHER INFORMATION: synthetic peptide

<400> SEQUENCE: 27

Leu Ala Asn Tyr Thr Gln Thr Lys Thr Val Ser Ile Arg Leu Gly Asp
1 5 10 15

Ala Leu Phe Gly
20

<210> SEQ ID NO 28
<211> LENGTH: 9
<212> TYPE: PRT
<213> ORGANISM: Artificial Sequence
<220> FEATURE:

-continued

<223> OTHER INFORMATION: synthetic peptide

<400> SEQUENCE: 28

Trp Lys Ile Gly Pro Ala Ile Ala Thr
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic peptide

<400> SEQUENCE: 29

Tyr Thr Gln Thr Lys Thr Val Ser Ile
1               5

<210> SEQ ID NO 30
<211> LENGTH: 14
<212> TYPE: PRT
<213> ORGANISM: Artificial Sequence
<220> FEATURE:
<223> OTHER INFORMATION: synthetic peptide

<400> SEQUENCE: 30

Val Ala Ile Thr Tyr Ala Ser Arg Ala Gln Gly Ala Glu Lys
1               5                   10

<210> SEQ ID NO 31
<211> LENGTH: 13
<212> TYPE: PRT
<213> ORGANISM: Artificial Sequence
<220> FEATURE:
<223> OTHER INFORMATION: synthetic peptide

<400> SEQUENCE: 31

Ala Glu Val Tyr Gln Lys Leu Lys Ser Leu Thr Lys Lys
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic peptide

<400> SEQUENCE: 32

Val Ala Ile Thr Tyr Ala Ser Arg Ala Gln Gly Ala Glu
1               5                   10

<210> SEQ ID NO 33
<211> LENGTH: 15
<212> TYPE: PRT
<213> ORGANISM: Artificial Sequence
<220> FEATURE:
<223> OTHER INFORMATION: synthetic peptide

<400> SEQUENCE: 33

Gly His His Phe Lys Glu Arg Gly Thr Gly Ser Leu Val Ile Thr
1               5                   10                  15

<210> SEQ ID NO 34
<211> LENGTH: 13
<212> TYPE: PRT
<213> ORGANISM: Artificial Sequence
<220> FEATURE:
<223> OTHER INFORMATION: synthetic peptide

<400> SEQUENCE: 34

Ala Asn Tyr Thr Gln Thr Lys Thr Val Ser Ile Arg Leu
1 5 10

<210> SEQ ID NO 35
<211> LENGTH: 13
<212> TYPE: PRT
<213> ORGANISM: Artificial Sequence
<220> FEATURE:
<223> OTHER INFORMATION: synthetic peptide

<400> SEQUENCE: 35

Gly Gly Tyr Lys Ala Ala Val Arg Pro Thr Met Leu Glu
1 5 10

<210> SEQ ID NO 36
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (11)..(11)
<223> OTHER INFORMATION: Xaa = Nle

<400> SEQUENCE: 36

Gly Gly Tyr Lys Ala Ala Val Arg Pro Thr Xaa Leu Glu
1 5 10

<210> SEQ ID NO 37
<211> LENGTH: 13
<212> TYPE: PRT
<213> ORGANISM: Artificial Sequence
<220> FEATURE:
<223> OTHER INFORMATION: synthetic peptide

<400> SEQUENCE: 37

Gly Leu Phe Ile Ser Thr Gly Thr Gln Gly Gly Gly Gln
1 5 10

<210> SEQ ID NO 38
<211> LENGTH: 17
<212> TYPE: PRT
<213> ORGANISM: Artificial Sequence
<220> FEATURE:
<223> OTHER INFORMATION: synthetic peptide

<400> SEQUENCE: 38

Ala Glu Val Tyr Gln Lys Leu Lys Ala Leu Ala Lys Lys Thr Tyr Gly
1 5 10 15

Gln

<210> SEQ ID NO 39
<211> LENGTH: 13
<212> TYPE: PRT
<213> ORGANISM: Artificial Sequence
<220> FEATURE:
<223> OTHER INFORMATION: synthetic peptide

<400> SEQUENCE: 39

Gly Trp Gly Val Met Val Ser His Arg Ser Gly Glu Thr
1 5 10

<210> SEQ ID NO 40

-continued

<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: Xaa = Nle

<400> SEQUENCE: 40

```
Gly Trp Gly Val Xaa Val Ser His Arg Ser Gly Glu Thr
1               5                   10
```

<210> SEQ ID NO 41
<211> LENGTH: 16
<212> TYPE: PRT
<213> ORGANISM: Artificial Sequence
<220> FEATURE:
<223> OTHER INFORMATION: synthetic peptide

<400> SEQUENCE: 41

```
Gly Tyr Thr Gly Lys Ile Lys Ile Ala Met Asp Val Ala Ser Ser Glu
1               5                   10                  15
```

<210> SEQ ID NO 42
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (10)..(10)
<223> OTHER INFORMATION: Xaa = Nle

<400> SEQUENCE: 42

```
Gly Tyr Thr Gly Lys Ile Lys Ile Ala Xaa Asp Val Ala Ser Ser Glu
1               5                   10                  15
```

<210> SEQ ID NO 43
<211> LENGTH: 14
<212> TYPE: PRT
<213> ORGANISM: Artificial Sequence
<220> FEATURE:
<223> OTHER INFORMATION: synthetic peptide

<400> SEQUENCE: 43

```
Leu Ala Ile Thr Tyr Asn Ser Arg Ala Glu Gly Ala Glu Lys
1               5                   10
```

<210> SEQ ID NO 44
<211> LENGTH: 15
<212> TYPE: PRT
<213> ORGANISM: Artificial Sequence
<220> FEATURE:
<223> OTHER INFORMATION: synthetic peptide

<400> SEQUENCE: 44

```
Gly Leu His Phe Arg Glu Arg Lys Thr Gly Ser Leu Val Ile Thr
1               5                   10                  15
```

<210> SEQ ID NO 45
<211> LENGTH: 14
<212> TYPE: PRT
<213> ORGANISM: Artificial Sequence
<220> FEATURE:
<223> OTHER INFORMATION: synthetic peptide -continued

<400> SEQUENCE: 45

Asn Glu Trp Arg Asp Phe Ala Arg Val Asn Ser Ile Ser Pro
1 5 10

<210> SEQ ID NO 46
<211> LENGTH: 14
<212> TYPE: PRT
<213> ORGANISM: Artificial Sequence
<220> FEATURE:
<223> OTHER INFORMATION: synthetic peptide

<400> SEQUENCE: 46

Lys Leu Trp His Ser Met Ile Pro Met Gly Arg Asp Ala Lys
1 5 10

<210> SEQ ID NO 47
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (6)..(6)
<223> OTHER INFORMATION: Xaa = Nle
<220> FEATURE:
<221> NAME/KEY: MOD_RES
<222> LOCATION: (9)..(9)
<223> OTHER INFORMATION: Xaa = Nle

<400> SEQUENCE: 47

Lys Leu Trp His Ser Xaa Ile Pro Xaa Gly Arg Asp Ala Lys
1 5 10

<210> SEQ ID NO 48
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (6)..(6)
<223> OTHER INFORMATION: Xaa = Nle

<400> SEQUENCE: 48

Lys Leu Trp His Ser Xaa Ile Pro Met Gly Arg Asp Ala Lys
1 5 10

<210> SEQ ID NO 49
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (9)..(9)
<223> OTHER INFORMATION: Xaa = Nle

<400> SEQUENCE: 49

Lys Leu Trp His Ser Met Ile Pro Xaa Gly Arg Asp Ala Lys
1 5 10

<210> SEQ ID NO 50
<211> LENGTH: 14
<212> TYPE: PRT
<213> ORGANISM: Artificial Sequence
<220> FEATURE:

<223> OTHER INFORMATION: synthetic peptide

<400> SEQUENCE: 50

```
Trp Ser Trp Lys Ile Gly Pro Ala Ile Ala Thr Gly Asn Thr
1               5                   10
```

<210> SEQ ID NO 51
<211> LENGTH: 15
<212> TYPE: PRT
<213> ORGANISM: Artificial Sequence
<220> FEATURE:
<223> OTHER INFORMATION: synthetic peptide

<400> SEQUENCE: 51

```
Ala Asn Glu Trp Arg Asp Phe Ala Arg Val Asn Ser Ile Ser Pro
1               5                   10                  15
```

<210> SEQ ID NO 52
<211> LENGTH: 13
<212> TYPE: PRT
<213> ORGANISM: Artificial Sequence
<220> FEATURE:
<223> OTHER INFORMATION: synthetic peptide

<400> SEQUENCE: 52

```
Ala Glu Val Tyr Gln Lys Leu Lys Ala Leu Ala Lys Lys
1               5                   10
```

<210> SEQ ID NO 53
<211> LENGTH: 33
<212> TYPE: PRT
<213> ORGANISM: Artificial Sequence
<220> FEATURE:
<223> OTHER INFORMATION: synthetic peptide

<400> SEQUENCE: 53

```
Glu Ser Asn Tyr Ser Ala Ile Val Glu Lys Gly Gly Tyr Lys Ala Ala
1               5                   10                  15

Val Arg Pro Thr Met Leu Glu Glu Ile Glu Ser Glu Ala Lys Val Ala
            20                  25                  30

Ser
```

<210> SEQ ID NO 54
<211> LENGTH: 13
<212> TYPE: PRT
<213> ORGANISM: Artificial Sequence
<220> FEATURE:
<223> OTHER INFORMATION: synthetic peptide

<400> SEQUENCE: 54

```
Leu Ala Ile Thr Tyr Asn Ser Arg Ala Glu Gly Ala Glu
1               5                   10
```

<210> SEQ ID NO 55
<211> LENGTH: 15
<212> TYPE: PRT
<213> ORGANISM: Artificial Sequence
<220> FEATURE:
<223> OTHER INFORMATION: synthetic peptide

<400> SEQUENCE: 55

```
Ala Lys Thr Ile Ala Tyr Asp Glu Glu Ala Arg Arg Gly Leu Glu
1               5                   10                  15
```

<210> SEQ ID NO 56

```
<211> LENGTH: 13
<212> TYPE: PRT
<213> ORGANISM: Artificial Sequence
<220> FEATURE:
<223> OTHER INFORMATION: synthetic peptide

<400> SEQUENCE: 56

Pro Lys Tyr Val Lys Gln Asn Thr Leu Lys Leu Ala Thr
1               5                   10


<210> SEQ ID NO 57
<211> LENGTH: 15
<212> TYPE: PRT
<213> ORGANISM: Artificial Sequence
<220> FEATURE:
<223> OTHER INFORMATION: synthetic peptide

<400> SEQUENCE: 57

Glu Asn Pro Val Val His Phe Phe Lys Asn Ile Val Thr Pro Arg
1               5                   10                  15
```

CLADOSPORIUM PEPTIDES

CROSS-REFERENCE TO RELATED APPLICATIONS

This application is a 35 U.S.C. 371 national stage filing of International Application PCT/GB2013/051440, filed May 30, 3013, which claims priority to Great Britain Patent Application No. 1209862.0, filed Jun. 1, 2012. The contents of the aforementioned applications are hereby incorporated by reference in their entirety.

FIELD OF THE INVENTION

The present invention relates to polypeptides and pharmaceutical formulations which may be used for preventing or treating allergy to moulds of the *Cladosporium* and/or *Alternaria* genus.

BACKGROUND TO THE INVENTION

Mould allergens are recognised as a major cause of allergic diseases in humans and animals, including asthma, allergic rhinitis, allergic conjunctivitis and allergic dermatitis. In colder climates, moulds can be found in the outdoor air starting in the late winter, and peaking in the late summer to early fall months (July to October). In warmer climates, mould spores may be found throughout the year, with the highest levels found in the late summer to early fall months. While indoor moulds can occur year round and are dependent on moisture levels in the home, indoor mould levels are higher when outdoor mould levels are higher. Therefore, a common source of indoor mould is from the outside environment, although can also be from indoor mould contamination.

There are thousands of types of mould; however, only a few of these are commonly associated with allergy. The following are the most likely causes of allergic disease based on the types of mould spores collected in the air: *Alternaria, Cladosporium, Aspergillus, Penicillium, Helminthosporum, Epicoccum, Fusarium, Aureobasidium, Phoma, Rhizopus, Mucor*, Smuts and Yeasts. Moulds in the genus *Alternaria*, in particular *Alternaria. alternata*, and the genus *Cladosporium* are considered to be among the most important allergenic fungi.

*Cladosporium* is the most common airborne outdoor mould. *Alternaria* is one of the main allergens affecting children. In temperate climates, airborne *Alternaria* spores are detectable from for most of the year (typically May to November in the northern hemisphere), with peaks in late summer and autumn. Dispersion of *Alternaria* spores occurs during dry periods. These feature higher wind velocity and lower relative humidity, which result in peak dispersion during sunny afternoon periods Although considered to be an outdoor mould, *Alternaria* will grow anywhere that provides sufficient moisture and a suitable growth substrate. Accordingly, *Alternaria* is commonly found indoors, in particular in damp areas such as basements, kitchens or bathrooms. *Alternaria* is commonly found in refrigerator drip trays, air conditioners, waste containers, mattresses, foam rubber pillows, or even in condensation on windows. It is one of the most common mould spores found in house dust in both North America and Europe. It is effectively impossible to avoid *Alternaria* allergens.

SUMMARY OF THE INVENTION

The invention provides a polypeptide, or a pharmaceutically acceptable salt thereof, suitable for use in preventing or treating allergy to *Cladosporium* and/or *Alternaria*, which is up to 30 amino acids in length and comprises:

(I) the amino acid sequence:

```
(a)  GGYKAAVRPTMLE,   (SEQ ID NO: 35; Cla35)

(b)  AEVYQKLKSLTKK,   (SEQ ID NO: 31; Cla16)

(c)  VAITYASRAQGAE,   (SEQ ID NO: 32; Cla25)

(d)  GHHFKERGTGSLVIT, (SEQ ID NO: 33; Cla26)
or

(e)  ANYTQTKTVSIRL;   (SEQ ID NO: 34; Cla29)
```

or (II) a T cell epitope-containing variant sequence which is a said amino acid sequence (I) having up to six amino acid modifications, each of which is independently a deletion, substitution or insertion.

The invention further provides a pharmaceutical formulation which comprises a pharmaceutically acceptable carrier or diluent and a polypeptide of the invention, or a pharmaceutically acceptable salt thereof.

The invention additionally provides a polypeptide, salt or pharmaceutical formulation of the invention for use in a method of treating or preventing allergy to *Cladosporium* and/or *Alternaria*.

The invention further provides a method of treating an individual for allergy to *Cladosporium* and/or *Alternaria* or of preventing in an individual allergy to *Cladosporium* and/or *Alternaria*, which method comprises administering to said individual a therapeutically or prophylactically effective amount of a polypeptide, salt or pharmaceutical formulation of the invention.

The invention also provides use of a polypeptide or salt of the invention for the manufacture of a medicament for the prevention or treatment of allergy to *Cladosporium* and/or *Alternaria*.

The invention additionally provides an in vitro method of determining whether T cells recognize a polypeptide or salt of the invention, which method comprises contacting said T cells with said polypeptide or salt and detecting whether said T cells are stimulated by said polypeptide or salt.

The invention further provides a method of preparing a pharmaceutical formulation of the invention, comprising combining one or more polypeptides or salts described herein with a pharmaceutically acceptable carrier or diluent.

DESCRIPTION OF THE SEQUENCES

SEQ ID NOS: 1 to 57 provide amino acid sequences as set out in Examples 1 to 7. In more detail:

SEQ ID NOS: 1 to 9 and 31 correspond to amino acid sequences derived from the protein Cla h6.

SEQ ID NO: 37 corresponds to an amino acid sequence derived from the protein Cla h7.

SEQ ID NOS: 10 to 20, 30, 32, 33 and 51 correspond to amino acid sequences derived from the protein Cla h8.

SEQ ID NOS: 21 to 29 and 34 correspond to amino acid sequences derived from the protein Cla h10.

SEQ ID NOS: 35, 36 and 53 correspond to amino acid sequences derived from the protein Cla c9.

SEQ ID NOS: 38 to 42 and 52 correspond to amino acid sequences derived from the protein Alt a6.

SEQ ID NOS: 43 to 49 and 54 correspond to amino acid sequences derived from the protein Alt a8.

SEQ ID NO: 50 corresponds to an amino acid sequence derived from the protein Alt al0.

SEQ ID NOS: 55 to 57 correspond to the amino acid sequences of control polypeptides used in Example 6.

NCBI or Uniprot accession numbers for the proteins referred to above are provided in Examples 1 to 7.

DETAILED DESCRIPTION OF THE INVENTION

The present invention is concerned with preventing or treating allergy to *Cladosporium* and/or *Alternaria* and provides polypeptides, and pharmaceutically acceptable salts thereof, suitable for this use. Said polypeptides or salts may be provided in pharmaceutical formulations.

Amino Acid Sequences and Variant Amino Acid Sequences

A polypeptide of the invention may comprise, consist or consist essentially of an amino acid sequence as shown in any one of SEQ ID NOs 31 to 35.

Alternatively, a polypeptide of the invention may comprise, consist or consist essentially of a T cell epitope-containing variant sequence which is an amino acid sequence as shown in any one of SEQ ID NOs 31 to 35 having up to six amino acid modifications, each of which is independently a deletion, substitution or insertion.

It is preferred that the modifications in a variant sequence do not alter the functional properties of a T cell epitope present in the corresponding original amino acid sequence. The functional properties of T cell epitopes are discussed further below. In preferred variant sequences, sufficient contiguous amino acids of the corresponding original amino acid sequence are retained to contain a T cell epitope. Typically, such a variant sequence retains at least 8, preferably at least 9, contiguous amino acids of the original amino acid sequence. The variant sequence may retain from 8 to 12 amino acids or from 9 to 12 amino acids of the original amino acid sequence.

A variant sequence may have fewer than six amino acid modifications. For example, said variant sequence may have up to five amino acid modifications, preferably up to four said amino modifications, more preferably up to three amino acid modifications, and most preferably only one or two amino acid modifications. All said modifications are independently a deletion, substitution or insertion.

In a particularly preferred embodiment, the variant sequence has one or two amino acid modifications, the or each of which independently is a deletion or substitution.

Deletions

Where a T cell epitope-containing variant sequence has an amino acid modification that is a deletion, the deleted amino acid is preferably removed from the N- or C-terminus of the corresponding original amino acid sequence. That is, the variant sequence is a truncation of the original amino acid sequence formed by removing one or more contiguous amino acids from the N- and/or C-terminus of the original sequence. Such a variant sequence may optionally have no other deletions or no other modifications.

A deleted amino acid may less preferably be removed from an internal position in the corresponding original amino acid sequence. By removal from an internal position it is meant that a deleted amino acid is not itself at the N- or C-terminus of the original amino acid sequence and nor is it removed as part of a sequence of contiguous amino acids including the N- or C-terminus of the original amino acid sequence. That is, to be considered to be deletion from an internal position, said deletion must occur independently of deletion from the N- or C-terminus of the original amino acid sequence.

For example, given an original sequence ABCDEFGH, an example variant sequence having an internal deletion of two amino acids could be ADEFGH, that is B and C are removed from internal positions and the original terminal residues A and H are retained. By contrast, a deletion of two contiguous amino acids from the N-terminus of the same original sequence would result in the variant sequence CDEFGH, in which A and B are removed and C is now at the N-terminus. The deletion of B in this case is not a removal from an internal position, because it is removed as one of the two contiguous amino acids including the N-terminus of the original sequence.

Where more than one deletion occurs in a variant sequence, the deleted amino acids may be removed from any combination of the N-terminus and/or the C-terminus and/or an internal position. Preferred variant sequences have no more than one deletion from an internal position. In particularly preferred variant sequences there is no deletion from an internal position, and the deleted amino acids are removed from any combination of the N- and/or C-terminus of the original sequence. That is, the deleted amino acids may all be removed from the N-terminus of the original sequence, or they may all be removed from the C-terminus of the original sequence, or some amino acids may be removed from each end of the original sequence.

Thus, in one embodiment, a variant sequence is an amino acid sequence of any one of SEQ ID NOs 31 to 35 having one, two, three, four, five, or six amino acids removed from the N-terminus of said sequence of SEQ ID NOs 31 to 35.

In another embodiment, a variant sequence is an amino acid sequence of any one of SEQ ID NOs 31 to 35 having one, two, three, four, five, or six amino acids removed from the C-terminus of said sequence of SEQ ID NOs 31 to 35.

In another embodiment, a variant amino acid sequence is an amino acid sequence of any one of SEQ ID NOs 31 to 35 having a number of amino acids removed from both the N- and C-terminus of said sequence, provided that said sequence has no more than six modifications in total. A preferred embodiment of such a variant sequence is an amino acid sequence of any one of SEQ ID NOs 31 to 35 having one, two or three amino acids removed from the N- and/or C-terminus of said sequence of SEQ ID NOs 31 to 35, and optionally no other modifications.

Specific examples of variant amino acid sequences which have at least one deletion include:

- the variant sequence YQKLKSLTK (SEQ ID NO: 6), which is the amino acid sequence of AEVYQKLKSLTKK (SEQ ID NO: 31) having three amino acids removed from the N-terminus and one amino acid removed from the C terminus;
- the variant sequence ITYASRAQG (SEQ ID NO: 13). which is the amino acid sequence of VAITYASRAQGAE (SEQ ID NO: 32) having two amino acids removed from both the N-terminus and the C terminus;
- the variant sequence ERGTGSLVI (SEQ ID NO: 14). which is the amino acid sequence of GHHFKERGTGSLVIT (SEQ ID NO: 33) having five amino acids removed from the N-terminus and one amino acid removed from the C terminus; and
- the variant sequence YTQTKTVSI (SEQ ID NO: 29), which is the amino acid sequence of ANYTQTKTVSIRL (SEQ ID NO: 34) having two amino acids removed from the N-terminus and two amino acids removed from the C terminus.

Substitutions

Where a T cell epitope-containing variant sequence has an amino acid modification that is a substitution, the substitution may occur at any position in the original amino acid sequence. It is preferred that said substitution does not introduce a proline or a cysteine. It is also preferred that said substitution is a conservative substitution.

By conservative substitution, it is meant that an amino acid may be substituted with any alternative amino acid having similar properties. The following is a non-exhaustive list of examples:

The amino acids with basic side chains, such as lysine, arginine or histidine, may each be independently substituted for each other.

The amino acids with acidic side chains, such as aspartate and glutamate, may each be independently substituted for each other, or for their amide derivatives, asparagine and glutamine. A glutamate or glutamine may also preferably be replaced with pyroglutamate. A variant sequence having pyroglutamate substituted for glutamate or glutamine is particularly preferred where said pyroglutamate will correspond to the N-terminus of a polypeptide of the invention which comprises, consists or consists essentially of the variant sequence. Polypeptides with pyroglutamate at the N-terminus typically have improved stability during manufacture.

The amino acids with aliphatic side chains, such as glycine, alanine, valine, leucine and isoleucine, may each be independently substituted for each other. Particularly preferred substitutions in this category are limited to the amino acids with smaller aliphatic side chains, that is glycine, alanine, valine, which may preferably each be independently substituted for each other.

Other preferred substitutions include the substitution of methionine with norleucine (Nle).

Additionally, in more general terms, a neutral amino acid may be substituted with another neutral amino acid, a charged amino acid may be substituted with another charged amino acid, a hydrophilic amino acid may be substituted with another hydrophilic amino acid, a hydrophobic may be substituted with another hydrophobic amino acid, a polar amino acid may be substituted with another polar amino acid, and an aromatic amino acid may be substituted with another aromatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Specific examples of variant amino acid sequences which have at least one substitution include:

the variant sequence AEVYQKLKALAKK (SEQ ID NO: 52) is the amino acid sequence of AEVYQKLKSLTKK (SEQ ID NO: 31) having two substitutions. The amino acid S at position 9 of SEQ ID NO: 31 is substituted with A, and the T at position 11 of SEQ ID NO: 31 is substituted with A. Other preferred variant sequences of SEQ ID NO: 31 include sequences with alternative, preferably similar, substitutions at positions 9 and 11. For example, instead of substituting with A, both the S and T amino acids at positions 9 and 11 could be independently replaced with G or V;

the variant sequence LAITYNSRAEGAE (SEQ ID NO: 54) is the amino acid sequence of VAITYASRAQGAE (SEQ ID NO: 32) having three substitutions. The amino acid V at position 1 of SEQ ID NO: 32 is substituted with L, the A at position 6 of SEQ ID NO: 32 is substituted with N, and the Q at position 10 of SEQ ID NO: 32 is substituted with E. Other preferred variant sequences of SEQ ID NO: 32 include sequences with alternative, preferably similar, substitutions at positions 1, 6 and 10. For example, instead of substituting L with V, the amino acid at position 1 could be replaced with G or A; instead of substituting A with N, the amino acid at position 6 could be replaced with Q, E or D; and instead of substituting Q with E, the amino acid at position 10 could be replaced with N or D;

the variant sequence GLHFRERKTGSLVIT (SEQ ID NO: 44) is the amino acid sequence of GHHFKERGTGSLVIT (SEQ ID NO: 33) having three substitutions. The amino acid H at position 2 of SEQ ID NO: 33 is substituted with L, the K at position 5 of SEQ ID NO: 33 is substituted with R, and the G at position 8 of SEQ ID NO: 33 is substituted with K. Other preferred variant sequences of SEQ ID NO: 33 include sequences with alternative, preferably similar, substitutions at positions 2, 5 and 8. For example, instead of substituting H with L, the amino acid at position 1 could be replaced with V, G or A; instead of substituting K with R, the amino acid at position 6 could be replaced with H; and instead of substituting G with K, the amino acid at position 10 could be replaced with H or R; and the variant sequence GGYKAAVRPT-Nle-LE (SEQ ID NO: 36) is the amino acid sequence of GGYKAAVRPTMLE (SEQ ID NO: 35) having one substitution. The amino acid M at position 11 of SEQ ID NO: 35 is substituted with Norleucine.

Insertions

Where a variant sequence has an amino acid modification that is an insertion, the added amino acid may be inserted at any position in the original amino acid sequence. It is preferred that the insertion does not introduce a proline or a cysteine.

Preferably, an amino acid may be inserted at the N-terminus and/or C-terminus of the original sequence. That is, the variant sequence is an extension of the original amino acid sequence formed by adding amino acids to the N- and/or C-terminus of the original sequence. Such a variant sequence may optionally have no other insertions or no other modifications.

Less preferably, an amino acid may be inserted at an internal position. By insertion at an internal position it is meant that an amino acid is inserted at any position which is C-terminal to the amino acid at the N-terminus of the original sequence, or that an amino acid is inserted at any position which is N-terminal to the amino acid at the C-terminus of the original sequence.

Where more than one insertion occurs in a variant sequence, the added amino acids may be inserted at any combination of the N-terminus and/or the C-terminus and/or an internal position. Preferred variant sequences have no more than one insertion at an internal position. In particularly preferred variant sequences there is no insertion at an internal position, and the added amino acids are inserted at any combination of the N- and/or C-terminus of the original sequence. That is, the added amino acids may all be inserted at the N-terminus of the original sequence, or they may all be inserted at the C-terminus of the original sequence, or some amino acids may be inserted at each end of the original sequence. That is, the added amino acids may be considered to extend the original sequence at the N- and/or C-terminus.

Thus, in one embodiment, a variant sequence is an amino acid sequence of any one of SEQ ID NOs 31 to 35 having one, two, three, four, five, or six amino acids inserted at the N-terminus of said sequence of SEQ ID NOs 31 to 35.

In another embodiment, a variant sequence is an amino acid sequence of any one of SEQ ID NOs 31 to 35 having one, two, three, four, five, or six amino acids inserted at the C-terminus of said sequence of SEQ ID NOs 31 to 35.

In another embodiment, a variant sequence is an amino acid sequence of any one of SEQ ID NOs 31 to 35 having a number of amino acids inserted at both the N- and C-terminus of said sequence of SEQ ID NOs 31 to 35, provided that said sequence has no more than six modifications in total. A preferred embodiment of such a variant sequence is an amino acid sequence of any one of SEQ ID NOs 31 to 35 having one, two or three amino acids inserted at the N- and/or C-terminus of said sequence of SEQ ID NOs 31 to 35, and optionally no other modifications.

A variant sequence having a charged amino acid inserted at the N- and/or C-terminus is particularly preferred where said charged amino acid will correspond to the N- and/or C-terminus of the polypeptide of the invention which comprises, consists or consists essentially of the variant sequence. Charged residues at the N- and/or C-terminus of a polypeptide can improve the solubility of a polypeptide. Preferred charged amino acids include lysine, arginine and histidine. Lysine is particularly preferred. Thus, a particularly preferred variant sequence is an amino acid sequence of any one of SEQ ID NOs 31 to 35 having one or more charged amino acids, preferably one or more lysine residues, inserted at the N- and/or C-terminus of said sequence of SEQ ID NOs 31 to 35.

A specific example of a variant amino acid sequence which has at least one insertion is:

- the variant sequence VAITYASRAQGAEK (SEQ ID NO: 30), which is the amino acid sequence of VAITYASRAQGAE (SEQ ID NO: 32) having a lysine inserted at the C terminus.

In some variant sequences there may be substitutions and insertions. For example:

- the variant sequence of LAITYNSRAEGAEK (SEQ ID NO: 43) is the sequence of SEQ ID NO: 32 having three substitutions as described above for SEQ ID NO: 54 and in addition having a lysine inserted at the C-terminus. Other variant sequences based on SEQ ID NO: 43 may have alternative, preferably similar substitutions as described above for SEQ ID NO: 54, as well as a lysine inserted at the C-terminus.

Polypeptides

A polypeptide of the invention is up to 30 amino acids in length and comprises, consists or consists essentially of an amino acid sequence or variant sequence as defined above.

Said polypeptide may preferably be up to 25 amino acids in length, more preferably up to 20 amino acids in length or up to 17 amino acids in length, and most preferably up to 15 amino acids in length. Put another way, the polypeptide may have a maximum length of 30, 25, 20, 17 or 15 amino acids.

A polypeptide of the invention is preferably at least 8 amino acids in length, more preferably at least 9 amino acids in length, most preferably at least 12 amino acids in length. Put another way, the polypeptide may have a minimum length of 8, 9, or 12 amino acids.

A polypeptide of the invention may be of a length defined by any combination of a said minimum and a said maximum length. For example, the polypeptide may be 8 to 30, 8 to 25, 8 to 20, 8 to 17 or 8 to 15 amino acids in length. The polypeptide may be 9 to 30, 9 to 25, 9 to 20, 9 to 17 or 9 to 15 amino acids in length. The polypeptide may be 12 to 30, 12 to 25, 12 to 20, 12 to 17 or 12 to 15 amino acids in length. A preferred polypeptide is of 9 to 30 amino acids in length, more preferably 9 to 20 amino acids in length. A particularly preferred polypeptide is of 12 to 17 amino acids in length.

A polypeptide of the invention may comprise an amino acid sequence or variant sequence as defined above. Therefore, said polypeptide may include additional amino acids which are not defined by said amino acid sequence or variant sequence. The additional amino acids may be described as flanking said amino acid sequence or variant sequence. That is, the additional amino acids are included at the N-terminus and/or C-terminus of said amino acid sequence or variant sequence.

Put another way, a polypeptide of the invention may have a sequence consisting of said amino acid sequence or variant sequence having an N-terminal and/or C-terminal extension of a number of amino acids. The maximum number of amino acids in the N-terminal and/or C-terminal extension is determined by the maximum length of the polypeptide, as defined above.

The amino acids in an N-terminal extension of a said amino acids sequence or variant sequence preferably correspond to the amino acids immediately N-terminal to the said amino acid sequence in the native sequence of the protein from which it derives.

The amino acids in a C-terminal extension of a said amino acid sequence or variant sequence preferably correspond to the amino acids immediately C-terminal to the said amino acid sequence in the native sequence of the protein from which it derives.

The N-terminal and/or C-terminal extension may be the one, two, three, four, five, six, seven, eight, nine or ten amino acids corresponding respectively to the one, two, three, four, five, six, seven, eight, nine or ten contiguous amino acids immediately N-terminal or C-terminal to said amino acid sequence in the sequence of the protein from which it derives.

That is, the N-terminal and/or C-terminal extension is of from one to ten amino acids corresponding respectively to the one to ten contiguous amino acids immediately N-terminal or C-terminal to the said amino acid sequence in the native sequence of the protein from which it derives.

Preferably, the N-terminal and/or C-terminal extension is of from one to six amino acids corresponding respectively to the one to six contiguous amino acids immediately N-terminal or C-terminal to the said amino.

More preferably, the N-terminal and/or C-terminal extension is of from one to four amino acids corresponding respectively to the one to four contiguous amino acids immediately N-terminal or C-terminal to the said amino.

Most preferably, the N-terminal and/or C-terminal extension is of from one to two amino acids corresponding respectively to the one to two contiguous amino acids immediately N-terminal or C-terminal to the said amino acid sequence.

Specific examples of polypeptides of the invention which include an N-terminal and/or C-terminal extension to an amino acid sequence or variant sequence include the following:

AEVYQKLKSLTKK (SEQ ID NO: 31) may have a C-terminal extension of one, two, three, four or five amino acids corresponding to the one, two, three, four or five contiguous amino acids immediately C-terminal to AEVYQKLKSLTKK in the native sequence of Cla h 6, that is the amino acids R, Y, G, Q and S. For example, where all five said contiguous amino acids are present, the polypeptide of the invention has the amino acid sequence of AEVYQKLKSLTKKRYGQS(SEQ ID NO:1; C-terminal extension is underlined).

AEVYQKLKALAKK (SEQ ID NO: 52) may have a C-terminal extension of one, two, three or four amino acids corresponding to the one, two, three or four contiguous amino acids immediately C-terminal to AEVYQKLKALAKK in the native sequence of Alt a 6, that is the amino acids T, Y, G and Q. For example, where all four said contiguous amino acids are present, the polypeptide of the invention has the amino acid sequence of AEVYQKLKALAKKTYGQ(SEQ ID NO:38; C-terminal extension is underlined).

VAITYASRAQGAE (SEQ ID NO: 32) may have a N-terminal extension of one, two, three, four, five, six or seven amino acids corresponding to the one, two, three, four, five, six or seven contiguous amino acids immediately N-terminal to VAITYASRAQGAE in the native sequence of Cla h 8, that is the amino acids C, A, E, M, G, A and A. It may also have a C-terminal extension of one, two or three amino acids corresponding to the one, two or three contiguous amino acids immediately C-terminal to VAITYASRAQGAE in the native sequence of Cla h 8. That is the amino acids E, N and V. For example, where all seven contiguous amino acids are present in the N-terminal extension and all three contiguous amino acids are present in the C-terminal extension the polypeptide of the invention has the amino acid sequence of CAEMGAAVAITYASRAQGAEENV(SEQ ID NO:10; N and C-terminal extensions are underlined).

GHHFKERGTGSLVIT (SEQ ID NO: 33) may have a C-terminal extension of one, two, three, four, five, six, seven, eight, nine or ten amino acids corresponding to the one, two, three, four, five, six, seven, eight, nine or ten contiguous amino acids immediately C-terminal to GHHFKERGTGSLVIT in the native sequence of Cla h 8, that is the amino acids A, S, M, S, G, H, I, A, N and F. For example, where all ten said contiguous amino acids are present, the polypeptide of the invention has the amino acid GHHFKERGTGSLVIT ASMSGHIANF(SEQ ID NO:11, C-terminal extension underlined).

ANYTQTKTVSIRL (SEQ ID NO: 34) may have a N-terminal extension of one amino acid corresponding to the one amino acid immediately N-terminal to ANYTQTKTVSIRL in the native sequence of Cla h 10, that is the amino acid L. It may also have a C-terminal extension of one, two, three, four, five or six amino acids corresponding to the one, two, three, four, five or six contiguous amino acids immediately C-terminal to ANYTQTKTVSIRL in the native sequence of Cla h 10. That is the amino acids G, D, A, L, F and G. For example, where the one amino acid is present in the N-terminal extension and all six contiguous amino acids are present in the C-terminal extension the polypeptide of the invention has the amino acid sequence of LANYTQTKTVSIRLGDALFG(SEQ ID NO:27, N- and C-terminal extensions underlined).

GGYKAAVRPTMLE (SEQ ID NO: 35) may have a N-terminal extension of one, two, three, four, five, six, seven, eight, nine or ten amino acids corresponding to the one, two, three, four, five, six, seven, eight, nine or ten contiguous amino acids immediately N-terminal to GGYKAAVRPTMLE in the native sequence of Cla c 9, that is the amino acids E, S, N, Y, S, A, I, V, E and K. It may also have a C-terminal extension of one, two, three, four, five, six, seven, eight, nine or ten amino acids corresponding to the one, two, three, four, five, six, seven, eight, nine or ten contiguous amino acids immediately C-terminal to GGYKAAVRPTMLE in the native sequence of Cla c 9, that is the amino acids E, I, E, S, E, A, K, V, A and S. For example, where all ten contiguous amino acids are present in the N-terminal extension and all ten contiguous amino acids are present in the C-terminal extension the polypeptide of the invention has the amino acid sequence of ESNYSAIVEKGGYKAAVRPTMLE EIESEAKVAS(SEQ ID NO: 53; N- and C-terminal extensions underlined).

The amino acids in the N-terminal and/or C-terminal extension may not correspond exactly to amino acids in the native sequence of the protein from which an amino acid sequence or variant sequence derives. The N-terminal and/or C-terminal extension may include a sequence derived from said native sequence which has been modified, for example to improve stability, solubility or manufacturability of the polypeptide. For example, a methionine in the native sequence may be substituted with nor-leucine, and/or one or more charged residues may be added at the N-terminus of a N-terminal extension and/or the C-terminus of a C-terminal extension. Preferably positively charged residues such as arginine and lysine are added. Amino acids selected from histidine, glutamate and aspartate may be added.

Alternatively, the amino acids of an N-terminal and/or C-terminal extension may not correspond to amino acids in native sequence of the protein from which an amino acid sequence or variant sequence derives. They may instead be any suitable amino acids, preferably selected to improve stability, solubility or manufacturability of the polypeptide. For example, one or more charged residues may be added at the N and/or C terminus of any of SEQ ID NOS: 31 to 35. Preferably positively charged residues such as arginine and lysine are added. Amino acids selected from histidine, glutamate and aspartate may be added.

Additional polypeptides disclosed herein include, for example, polypeptides comprising, consisting or consisting essentially of an amino acid sequence of any one of SEQ ID NOs 2 to 5, 7 to 9, 12, 15 to 26, 28, 37, 39 to 42 and 45 to 51, or a variant sequence derived therefrom. The variant sequences referred to in this paragraph are derived from each corresponding original amino acid sequence in the same manner as is described above with respect to variant sequences derived from SEQ ID NOS: 31 to 35.

T Cell Epitopes

A polypeptide of the invention is up to 30 amino acids in length and comprises, consists or consists essentially of an amino acid sequence or variant sequence as defined above. Each said amino acid sequence and said variant sequences contains a T cell epitope. The T cell epitope is preferably an MHC Class II-binding T cell epitope. It is preferred that the modifications in a variant sequence do not alter the functional properties of a T cell epitope present in the corresponding original amino acid sequence.

In preferred variant sequences, sufficient contiguous amino acids of the corresponding original amino acid sequence are retained to contain a T cell epitope. Typically, such a variant sequence retains at least 8, preferably at least 9, contiguous amino acids of the original amino acid sequence The presence of a T cell epitope may preferably be confirmed by analysis performed in silico, for example using bioinformatic software as described in Examples 1 to 5. Alternatively, the presence of a T cell epitope may be confirmed by direct evaluation of its functional properties. Particular functional properties of T cell epitopes include the ability of a polypeptide comprising the epitope to bind to an MHC molecule, preferably an MHC Class II molecule, and/or the ability of a polypeptide comprising the epitope to activate a T cell, preferably when bound to an MHC Class II molecule.

The ability of a polypeptide to bind to an MHC molecule may be evaluated using any suitable method, such as a competition assay. A preferred in vitro assay is described in Example 6.

The ability of a polypeptide to activate a T cell may also be evaluated using any suitable method. Preferred methods include the measurement of one or more parameters associated with T cell activation, such as proliferation or cytokine release. Preferred assays for these parameters are described in Example 7. Relevant cytokines include IFN-gamma, IL-13 and IL-10. In the context of the present invention, a polypeptide is typically considered to have activated a T cell if it induces release of one, two, or all of IFN-gamma, IL-13 and IL-10. The polypeptide preferably induces a release of greater than 50 pg/ml of the given cytokine(s).

As mentioned above, it is preferred that the modifications in a variant sequence do not alter the functional properties of a T cell epitope present in the corresponding original amino acid sequence. Thus, a polypeptide comprising, consisting or consisting essentially of a variant amino acid sequence should have substantially the same MHC class II binding properties and substantially the same T cell activation properties as a polypeptide comprising, consisting or consisting essentially of the corresponding original amino acid sequence.

Typically, a polypeptide has substantially the same MHC Class II binding characteristics as another polypeptide if both polypeptides are capable of binding specifically to one or more MHC Class II molecules belonging to the same MHC Class II allele supertype family. Examples of MHC Class II allele supertype families include HLA-DR1, HLA-DR3, HLA-DR4, HLA-DR7, HLA-DR8, HLA-DR11, HLA-DR13, HLA-DR15 and HLA-DR51. Most preferably, both polypeptides will bind specifically to the same MHC Class II molecule, that is to an MHC Class II molecule encoded by the same allele.

Typically, a polypeptide has substantially the same T cell activation properties as another polypeptide if both polypeptides specifically activate a T cell expressing the same T cell receptor. Preferably, there should be no significant difference in the level of activation induced by each polypeptide. The level of activation may be assessed by monitoring proliferation and/or cytokine release, as described above.

Suitable polypeptides comprising, consisting or consisting essentially a variant sequence may be derived empirically or selected according to known criteria. Within a single polypeptide there are certain residues which contribute to binding within the MHC antigen binding groove and other residues which interact with hypervariable regions of the T cell receptor (Allen et al (1987) Nature 327: 713-5). Advantageously, peptides may be designed to favour T-cell proliferation and induction of desensitisation. Metzler and Wraith have demonstrated improved tolerogenic capacity of polypeptides in which substitutions increasing polypeptide-MHC affinity have been made (Metzler & Wraith (1993) Int Immunol: 1159-65). That an altered polypeptide ligand can cause long-term and profound anergy in cloned T cells was demonstrated by Sloan-Lancaster et al (1993) Nature 363: 156-9.

Sequence Identity

T cell epitope-containing variant sequences of the invention may alternatively be described in terms of their sequence identity to a corresponding original amino acid sequence. For example, a variant sequence may have at least 65% identity to an amino acid sequence of any one of SEQ ID NOS: 31 to 35. More preferably, a variant sequence may have at least 70%, at least 75%, at least 80%, at least 85%, at least 90%, or at least 95% amino acid identity to an amino acid sequence of any one of SEQ ID NOS: 31 to 35.

Sequence identity is typically evaluated over a number of contiguous amino acids in the original amino acid sequence. For example, sequence identity may be measured over at least 9, 10, 11, 12, 13, 14, or 15 contiguous amino acids in the original amino acid sequence, depending on the size of the peptides of comparison. It is preferred that sequence identity be measured over at least 9 contiguous amino acids in the original amino acid sequence. It is particularly preferred that sequence identity is measured over the entire length of the corresponding original amino acid sequence.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K, and R. Sequence identity at a particular residue is intended to include identical residues which have simply been derivatized.

Salts

The invention encompasses any pharmaceutically acceptable salt of a polypeptide of the invention. Pharmaceutically acceptable salts of a polypeptide of the invention include, for example, mineral acid salts such as chlorides, hydrochlorides, hydrobromides, phosphates, sulfates, and the like; and the salts of organic acids such as acetates, propionates, malonates, benzoates, and the like. A hydrochloride salt or an acetate salt is preferred.

Synthesis

A polypeptide of the invention can be prepared by any suitable technique. Solid-phase peptide synthesis (SPPS) is a preferred technique. This involves formation of the peptide on small solid beads.

Using SPPS, the peptide remains covalently attached to a bead during synthesis. The peptide is synthesised using repeated cycles of coupling-washing-deprotection-washing. In particular, the free N-terminal amine of a solid-phase attached peptide is coupled to a single N-protected amino acid unit. This unit is then deprotected, revealing a new N-terminal amine to which a further protected amino acid is attached. These steps are repeated until the peptide is complete. The peptide is then cleaved from the beads using a suitable reagent.

Suitable protecting groups, reagents, solvents and reaction conditions for SPPS are well known to those skilled in the art and as such conditions can be determined by one skilled in the art by routine optimization procedures.

Pharmaceutically acceptable salts of polypeptides can be prepared by any suitable technique. Typically, salification involves reaction of the polypeptide or a salt thereof with a suitable reagent, typically acid, to obtain the pharmaceutically acceptable salt selected.

For example, a hydrochloride salt of a polypeptide can be prepared by initially cleaving the polypeptide from the solid phase using trifluoroacetic acid. The polypeptide will thus initially be a trifluoroacetate salt. The trifluoroacetate salt can then be converted into a hydrochloride salt by any known technique, such as ion exchange on a suitable column using hydrochloric acid as an eluent.

The polypeptide or polypeptide salt products can be purified, where required, by any suitable technique. High pressure liquid chromatography (HPLC) can be used, for example.

The term "polypeptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopolypeptides containing changes involving the backbone, and not the orientation of side chains. Meziere et al (1997) show that, at least for MHC class II and T helper cell responses, these pseudopolypeptides are useful. Retro-inverse polypeptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the polypeptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups ($—NH_2 \rightarrow —NH(Me)$ or $—N(Me)_2$).

Analogues of polypeptides according to the invention may also include peptide variants that increase or decrease the polypeptide's half-life in vivo. Examples of analogues capable of increasing the half-life of polypeptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The polypeptides provided by the present invention may be derived from splice variants of the parent proteins encoded by mRNA generated by alternative splicing of the primary transcripts encoding the parent protein chains. The polypeptides may also be derived from amino acid mutants, glycosylation variants and other covalent derivatives of the parent allergen proteins. Exemplary derivatives include molecules wherein the polypeptides of the invention are covalently modified by substitution, chemical, enzymatic, or other appropriate means with a moiety other than a naturally occurring amino acid. Further included are naturally occurring variant amino acid sequences of the parent proteins. Such a variant amino acid sequence may be encoded by an allelic variant or represent an alternative splicing variant.

Modifications as described above may be prepared during synthesis of the peptide or by post-production modification, or when the polypeptide is in recombinant form using the known techniques of site-directed mutagenesis, random mutagenesis, or enzymatic cleavage and/or ligation of nucleic acids.

The polypeptides described herein may also be modified to improve physicochemical characteristics. Thus, for example, original amino acid sequences may be altered to improve their solubility, and accordingly a polypeptide of the invention having a variant sequence will preferably be more soluble than a polypeptide having the corresponding original amino acid sequence under equivalent conditions. Methods for evaluating the solubility of polypeptides are well known in the art.

Improved solubility is advantageous for the tolerisation of subjects to allergens from which the polypeptides of the invention derive, since administration of poorly soluble agents to subjects causes undesirable, non-tolerising inflammatory responses. The solubility of the polypeptides may be improved by altering the residues which flank the region containing a T cell epitope. For example, N and C terminal to the residues of the polypeptide which flank a T cell epitope, at least one amino acid may be added selected from arginine, lysine, histidine, glutamate and aspartate. In other examples:

i) any hydrophobic residues in the up to three amino acids at the N or C terminus of the native sequence of the polypeptide, which are not comprised in a T cell epitope, are deleted; and/or ii) any two consecutive amino acids comprising the sequence Asp-Gly in the up to four amino acids at the N or C terminus of the native sequence of the polypeptide, which are not comprised in a T cell epitope, are deleted; and/or iii) one or more positively charged residues are added at the N and/or C terminus of the native sequence of the polypeptide.

Optionally, any polypeptides containing cysteine residues may be engineered to prevent dimer formation such that any cysteine residues are replaced with serine or 2-aminobutyric acid.

Polypeptide Combinations

A polypeptide of the invention, or salt thereof, may be provided in combination with one or more further polypeptides, or salts thereof, of the invention. Accordingly, two, three, four, or five polypeptides or salts thereof may be provided together in combination. For example, a suitable combination may comprise two, three, four or five different polypeptides selected from the following:

i) a polypeptide comprising, consisting or consisting essentially of the amino acid sequence of SEQ ID NO: 35 or a said variant sequence derived therefrom, or a said salt thereof;

ii) a polypeptide comprising, consisting or consisting essentially of the amino acid sequence of SEQ ID NO: 31 or a said variant sequence derived therefrom, or a said salt thereof;

iii) a polypeptide comprising, consisting or consisting essentially of the amino acid sequence of SEQ ID NO: 32 or a said variant sequence derived therefrom, or a said salt thereof;

iv) a polypeptide comprising, consisting or consisting essentially of the amino acid sequence of SEQ ID NO: 33 or a said variant sequence derived therefrom, or a said salt thereof; and v) a polypeptide comprising, consisting or consisting essentially of the amino acid sequence of SEQ ID NO: 34 or a said variant sequence derived therefrom, or a said salt thereof.

It is preferred that the combination should include no more than one polypeptide, or salt thereof, selected from each of i) to v). It is particularly preferred that the combination includes at least one polypeptide, or salt thereof, selected from i).

A combination as defined above may further include one or more additional polypeptides. Additional polypeptides disclosed herein include, for example, polypeptides comprising, consisting or consisting essentially of an amino acid sequence of any one of SEQ ID NOs 2 to 5, 7 to 9, 12, 15 to 26, 28, 37, 39 to 42 and 45 to 51, or a variant sequence derived therefrom. In some embodiments, the further polypeptides in a combination are selected only from polypeptides which comprise, consist or consist essentially of an amino acid sequence of any one of SEQ ID NOs: 1 to 29, 37, 51 and 53 (which are derived directly from *Cladosporium* allergens), or a variant sequence derived therefrom. In other embodiments, the further polypeptides may comprise, consist or consist essentially of an amino acid sequence of any one of SEQ ID NOs: 1 to 29 and 37 to 54, or a variant sequence derived therefrom. The variant sequences referred to in this paragraph are derived from each corresponding original amino acid sequence in the same manner as is described above with respect to variant sequences derived from SEQ ID NOS: 31 to 35.

Preferably, a combination will include a polypeptide comprising, consisting or consisting essentially of a first amino acid sequence (or variant derived therefrom) and at least one further polypeptide comprising, consisting or consisting essentially of a second amino acid sequence (or variant derived therefrom), wherein said second amino acid sequence derives from a different allergen to said first amino acid sequence. The allergens from which each of the amino acid sequences disclosed herein derive are set out in the section entitled "Description of Sequences" above. By including sequences which derive from more than one Cla (and/or Alt) allergen, a combination may allow for broad coverage of mould allergy observed in the general population by providing T cell epitopes from more than one mould allergen.

Particularly preferred combinations include at one, two or three further polypeptides selected from:

```
(f)  GWGVMVSHRSGET;     (SEQ ID NO: 39; Alt14)

(g)  GYTGKIKIAMDVASSE,  (SEQ ID NO: 41; Alt15)
and

(h)  WSWKIGPAIATGNT.    (SEQ ID NO: 50; Alt28)
```

Any of the polypeptide combinations described above may optionally comprise no further polypeptides, or no further polypeptides derived from *Alternaria* and/or *Cladosporium* allergens. Any of the polypeptide combinations described above may be incorporated in a pharmaceutical formulation of the invention as described in more detail below.

Medical Uses and Methods

A preferred aspect of the invention is the prevention or treatment of allergy. In this aspect, the invention provides a polypeptide or salt of the invention or a pharmaceutical formulation of the invention for use in a method of treating or preventing allergy to *Cladosporium* and/or *Alternaria*. The polypeptide, salt or pharmaceutical formulation of the invention may prevent or treat the allergy by tolerisation. The tolerisation may be to one or more protein allergens of the *Cladosporium* and/or *Alternaria* genus.

The invention further provides a use of a polypeptide or salt of the invention for the manufacture of a medicament for the prevention or treatment of allergy to *Cladosporium* and/or *Alternaria*.

The invention further provides a method of treating an individual for allergy to *Cladosporium* and/or *Alternaria* or of preventing in an individual allergy to *Cladosporium* and/or *Alternaria*, which method comprises administering to said individual a therapeutically or prophylactically effective amount of a polypeptide or salt of the invention or of a pharmaceutical formulation of the invention. The method may thus reduce or ameliorate the symptoms of allergy in the individual suffering from the allergy. The method may improve the condition of the individual suffering from the allergy. The method may prevent or delay the appearance of symptoms of allergy in the individual. Symptoms of allergy to mould are discussed below.

In each of the methods and uses mentioned in this section, a polypeptide or salt may be replaced with a combination of polypeptides or salts as was defined in the previous section. As such, the invention encompasses a scenario in which a combination of polypeptides or salts is used in a method of treating or preventing allergy to *Cladosporium* and/or *Alternaria*. In said scenario, the polypeptides in a combination need not be administered together, and/or need not be not part of the same pharmaceutical formulation.

The invention thus provides a polypeptide or salt of the invention for use in a method of preventing or treating allergy to *Cladosporium* and/or *Alternaria* as described above, wherein said method further comprises administering at least one, preferably two or more additional polypeptides of the invention. The multiple peptides of this method may each be administered simultaneously, sequentially or concurrently.

The polypeptide, salt or pharmaceutical formulation of the invention may treat or prevent the allergy by desensitising or tolerising to *Cladosporium* and/or *Alternaria* allergens. A polypeptide of the invention may be used to tolerise or desensitise an individual to the allergen from which it is derived. Desensitising an individual to the allergens means inhibition or dampening of allergic tissue reactions induced by the allergens in appropriately sensitised individuals. The term "tolerisation" refers to an ability to suppress, or abolish a response to an antigen, such as an allergic response to a protein allergen. Tolerisation is also an ability to diminish or abolish an unwanted immune response, or to desensitise a subject to a protein allergen. Tolerisation may be determined by in vitro analysis of T cell responses or by observation of a reduction in the symptoms in an individual.

In more detail, T cells can be selectively activated, and then rendered unresponsive. Moreover the anergising or elimination of these T-cells leads to desensitisation of the patient for a particular allergen. The desensitisation manifests itself as a reduction in response to an allergen or allergen-derived peptide, or preferably an elimination of such a response, on second and further administrations of the allergen or allergen-derived peptide. This second administration may be made after a suitable period of time has elapsed to allow desensitisation to occur; this is preferably any period between one day and several weeks. An interval of around four weeks is preferred.

The individual to whom the polypeptide, salt or pharmaceutical formulation is administered may be asymptomatic. A prophylactically effective amount of the polypeptide or pharmaceutical formulation is administered to such an individual. A prophylactically effective amount is an amount which prevents the onset of one or more symptoms of allergy.

Alternatively, the individual to whom the polypeptide, salt or pharmaceutical formulation is administered may be in need thereof. That is, the individual may exhibit one or more symptoms of allergy. A therapeutically effective amount of the polypeptide or pharmaceutical formulation is administered to such an individual. A therapeutically effective amount is an amount which is effective to ameliorate one or more symptoms of allergy.

The individual to whom the polypeptide, salt or pharmaceutical formulation is administered is preferably human. The individual may be known to be sensitised to mould allergens, at risk of being sensitised or suspected of being sensitised. The individual can be tested for sensitisation using techniques well known in the art and as described herein. Alternatively, the individual may have a family history of allergy to mould.

It may not be necessary to test an individual for sensitisation to mould because the individual may display symptoms of allergy when exposed to mould. By exposure is meant proximity to, for example, a mould or a substance or product derived from a mould. By proximity is meant 10 metres or less, 5 metres or less, 2 metres or less, 1 metre or less, or 0 metres from the items described above. Symptoms of allergy can include an itching nose, sneezing, ocular tearing, an itchy throat, itchy palate, itchy eyes, runny nose, breathing difficulties, bronchospasm, asthma, red itchy skin or rash.

The individual may be of any age. However, preferably, the individual may be in the age group of 1 to 90, 5 to 60, 10 to 40, or more preferably 18 to 35.

Preferably, the individual is from a population that has MHC allele frequencies within the range of frequencies that are representative of the Caucasian population. Reference population allele frequencies for 11 common DRB 1 allele families are shown in Table 1 (Data from HLA Facts Book, Parham and Barber).

TABLE 1

| DRB1 | 1 | 3 | 4 | 7 | 8 | 11 | 12 | 13 | 14 | 15 | 16 |
|---|---|---|---|---|---|---|---|---|---|---|---|
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:

4—at least 9%

7—at least 10%

11—at least 8%.

The individual may have had allergy to mould for at least 2 weeks, 1 month, 6 months, 1 year, 5 years or more than 5 years. The individual may suffer from a rash, nasal congestion, nasal discharge and/or coughing caused by the allergy. The individual may or may not have been administered with other compositions/compounds which treat mould allergy. The individual may live in a geographical region which has a temperate, semi-tropical, tropical, or arctic climate. The individual typically suffers from allergy to mould in a particular season but the allergy may be perennial. Seasonal allergy to mould may commonly occur in autumn in the Northern hemisphere.

The allergic individual is typically allergic to moulds of the *Cladosporium* genus, particularly *Cladosporium* herbarium and/or *Cladosporium* cladosporoides. The allergic individual may be allergic to moulds of the *Alternaria* genus, particularly *Alternaria alternata*. The allergic individual may be allergic both to moulds of the *Cladosporium* and *Alternata* genus.

The polypeptides, salts or pharmaceutical formulations of the invention may be screened in panels of mould allergic individuals to confirm their suitability for use. The panel of mould allergic individuals may comprise individuals known or not known to be allergic to moulds of the *Alternaria* and *Cladosporium* genus. In particular where multiple polypeptides are provided in combination in a pharmaceutical formulation, they may be screened for their ability to cause T cell proliferation in at least 20% of samples of T cells, wherein each sample is obtained from different mould allergic individuals in the population. Preferably, the pharmaceutical formulation will induce T cell proliferation in at least 30% of samples of T cells obtained from of a panel of mould allergic individuals. More preferably, the pharmaceutical formulation will induce T cell proliferation in 35% or more, 40% or more, 50% or more, 60% or more, 70% or more, 80% or more, or 90% or more of samples in the panel. The number of individuals in a panel of mould allergic individuals may be any number greater than one, for example at least 2, 3, 5, 10, 15, 20, 30, 50, 80, or at least 100 individuals.

It is also preferred that the polypeptides, salts and pharmaceutical formulations of the invention cause T cell proliferation, but do not lead to the release of histamine from leucocyte samples from a sensitised individual. The histamine release profile of a polypeptide, salt or pharmaceutical formulation may thus be confirmed. Suitable leucocyte samples include enriched basophils or mast cell preparations. There may be some histamine release, but preferably the amounts released are not significant. Significant histamine release may be considered to be the release of 20% or more of the total available leukocyte histamine when a sample of leukocytes from an individual is stimulated with a pharmaceutical formulation in vitro. A polypeptide, salt or pharmaceutical formulation of the invention preferably causes the release of less than 5%, less than 4%, less than 3%, less than 2% or less than 1% of the total available leukocyte histamine when a sample of leukocytes from an individual is stimulated with a composition in vitro. A normal individual typically has an approximate leukocyte histamine content of 150 ng/$10^7$ cells.

Pharmaceutical Formulations

Each polypeptide or salt of the invention may be provided to an individual in an isolated, substantially isolated, purified or substantially purified form. For example, a polypeptide or salt of the invention may be provided to an individual substantially free from other polypeptides or salts thereof. Whilst it may be possible for the polypeptides or salts to be presented in raw form, it is preferable to present them as a pharmaceutical formulation.

Thus, according to a further aspect of the invention, the invention further provides a pharmaceutical formulation which comprises a pharmaceutically acceptable carrier or diluent and a polypeptide, or a pharmaceutically acceptable salt thereof, of the invention. The pharmaceutical formulation may comprise any combination of polypeptides or salts of the invention as described above.

The carrier(s) or diluent(s) present in the pharmaceutical formulation must be "acceptable" in the sense of being compatible with the other ingredients of the formulation and not deleterious to the recipient thereof. Typically, carriers for injection, and the final formulation, are sterile and pyrogen free. Preferably, the carrier or diluent is water. The carrier or diluent may comprise thioglycerol,thioanisole or methionine.

A composition containing one or more polypeptides or salts of the invention can be combined with one or more pharmaceutically acceptable excipients or vehicles to produce a pharmaceutical formulation. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

The polypeptide or salt is typically present at 0.1% to 50% by weight in the pharmaceutical formulation, more preferably at 0.1% to 5% by weight. The polypeptide or salt may be present at less than 0.1% by weight in the pharmaceutical formulation.

The pharmaceutically acceptable carrier or diluent is typically present at 50% to 99.9% by weight in the pharmaceutical formulation, more preferably at 95% to 99.9% by weight. The pharmaceutically acceptable carrier or diluents may be present at more than 99.9% by weight in the pharmaceutical formulation.

Pharmaceutical formulations include, but are not limited to pharmaceutically acceptable solutions, lyophilisates, suspensions, emulsions in oily or aqueous vehicles, pastes, and implantable sustained-release or biodegradable formulations. Such pharmaceutical formulations may further comprise one or more additional ingredients including, but not limited to, suspending, stabilizing, or dispersing agents. A lyophilisate may comprise one or more of trehalose, thioglycerol, methionine and thioanisole. In one embodiment of a pharmaceutical formulation for parenteral administration, the active ingredient is provided in dry form (e.g., a lyophilisate, powder or granules) for reconstitution with a suitable vehicle (e. g., sterile pyrogen-free water) prior to parenteral administration of the reconstituted pharmaceutical formulation.

The invention further provides a method of preparing a pharmaceutical formulation of the invention, comprising combining a polypeptide or salt as described above, or a combination of polypeptide of polypeptides and salts as described above, with a pharmaceutically acceptable carrier or diluent. Preferably, said method prepares a pharmaceutical formulation for parenteral administration, and comprises providing said polypeptide(s), or salt(s) in dry form and reconstituting said polypeptide(s), or salt(s) with a said pharmaceutically acceptable carrier or diluent.

The pharmaceutical formulations may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parenterally-administrable pharmaceutical formulations which are useful include those which comprise the active ingredient in microcrystalline form, in a liposomal preparation, or as a component of a biodegradable polymer systems. pharmaceutical formulations for sustained release or implantation may comprise pharmaceutically acceptable polymeric or hydrophobic materials such as an emulsion, an ion exchange resin, a sparingly soluble polymer, or a sparingly soluble salt.

Alternatively, the polypeptides of the present invention may be encapsulated, adsorbed to, or associated with, particulate carriers. Suitable particulate carriers include those derived from polymethyl methacrylate polymers, as well as PLG microparticles derived from poly(lactides) and poly (lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the polypeptides mentioned herein will depend upon factors such as the nature of the polypeptide and the method of delivery. The pharmaceutical formulation may be administered in a variety of dosage forms. It may be administered orally (e.g. as tablets, troches, lozenges, aqueous or oily suspensions, dispersible powders or granules), topically, parenterally, subcutaneously, by inhalation, intravenously, intramuscularly, intralymphatically (such as to lymph nodes in the groin), intrasternally, transdermally, intradermally, epidermally, sublingually, intranasally, buccally or by infusion techniques. The administration may be intratonsillar. The administration may be as suppositories. The administration may be made by iontophoresis. Preferably, the administration is intradermal, epidermal or transdermal. The administration may be made by a patch, such as a microtine patch.

A physician will be able to determine the required route and means of administration for each particular individual.

The pharmaceutical formulations of the invention are preferably provided sealed in a container. Where the pharmaceutical formulation is a pharmaceutically acceptable solution, the solution may be provided in an ampoule, sealed vial, syringe, cartridge, flexible bag or glass bottle. Where the pharmaceutical formulation is a lyophilisate, it is preferably provided in a sealed vial.

The pharmaceutical formulations of the invention will comprise a suitable concentration of each polypeptide to be effective without causing adverse reaction. Where the pharmaceutical formulation is for example a lyophilisate, the relevant concentration will be that of each polypeptide following reconstitution. Typically, the concentration of each polypeptide in the pharmaceutical formulation when in solution will be in the range of 0.03 to 200 nmol/ml. The concentration of each polypeptide may be more preferably in the range of 0.3 to 200 nmol/ml, 3 to 180 nmol/ml, 10 to 150 nmol/ml, 50 to 200 nmol/ml or 30 to 120 nmol/ml. The pharmaceutical formulation should have a purity of greater than 95% or 98% or a purity of at least 99%.

An adjuvant or further therapeutic agent may be used in combination with one or more polypeptides of the invention. An adjuvant is preferably administered in an amount which is sufficient to augment the effect of the polypeptide(s) of the invention or vice versa. The adjuvant or further therapeutic agent may be an agent that potentiates the effects of a polypeptide of the invention. For example, the further therapeutic agent may be an immunomodulatory molecule which enhances the response to the polypeptide of the invention. Non-limiting examples of adjuvants include vitamin D, rapamycin and glucocorticoid steroids such as dexamethasone, fluticasone, budesonide, mometasone, beclomethasone, hydrocortisone, cortisone acetate, prednisone, prednisolone, methylprednisolone, betamethasone and triamcinolone. A preferred glucocorticoid is dexamethasone.

In an embodiment where one or more polypeptides of the invention are used for therapy in combination with one or more other therapeutic agents or adjuvants, the other therapeutic agents or adjuvants may be administered separately, simultaneously or sequentially. They may be administered in the same or different pharmaceutical formulations. A pharmaceutical formulation may therefore be prepared which comprises a polypeptide of the invention and also one or more other therapeutic agents or adjuvants. A pharmaceutical formulation of the invention may alternatively be used simultaneously, sequentially or separately with one or more other therapeutic compositions as part of a combined treatment. Accordingly, in a method of preventing or treating allergy according to the invention as described below, the subject may also be treated with a further therapeutic agent.

Routes of Administration

Where a polypeptide or salt of the invention is to be administered to an individual in a pharmaceutical formulation, it is preferred to administer the formulation to a site in the body of the individual where the polypeptide or salt will have the ability to contact suitable antigen presenting cells, and where it, or they, will have the opportunity to contact T cells of the individual.

Once formulated the pharmaceutical formulations of the invention can be delivered to a subject in vivo using a variety of known routes and techniques. For example, a pharmaceutical formulation can be provided as an injectable solution, suspension or emulsion and administered via parenteral, subcutaneous, epidermal, intradermal, intramuscular, intralymphatic, intraarterial, intraperitoneal, or intravenous injection using a conventional needle and syringe, a microneedle and syringe or using a liquid jet injection system. The administration may be made using a patch, such as a microtine patch. Compositions can also be administered topically to skin or mucosal tissue, such as nasally, intratonsillarly, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Dosages

Administration of the polypeptides, salts or pharmaceutical formulations of the invention may be by any suitable method as described above. Suitable amounts of the polypeptides or salts to be administered may be determined empirically, but typically are in the range given below. A single administration of each polypeptide or salt may be sufficient to have a beneficial effect for the patient, but it will be appreciated that it may be beneficial if the polypeptide or salt is administered more than once, in which case typical administration regimes may be, for example, once or twice a week for 2-4 weeks every 6 months, or once a day for a week every four to six months. As will be appreciated, each polypeptide or salt in a combination of polypeptides or salts may be administered to a patient singly or in combination.

Dosages for administration will depend upon a number of factors including the nature of the pharmaceutical formulation, the route of administration and the schedule and timing of the administration regime. Suitable doses of a polypeptide or salt of the invention may be in the order of up to 10 up to 15 μg, up to 20 μg, up to 25 μg, up to 30 μg, up to 50 μg, up to 100 m, up to 500 μg or more per administration. Suitable doses may be less than 15 μg, but at least 1 ng, or at least 2 ng, or at least 5 ng, or at least 50 ng, or least 100 ng, or at least 500 ng, or at least 1 μg, or at least 10 μg. For some polypeptides of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route. It will be understood that the above doses refer to total dose in the case of a combination of peptides or salts. For example, "up to 35 μg" refers to a total peptide or salt concentration of up to 35 μg in a composition comprising a combination or more than one peptide or salt.

Nucleic Acids and Vectors

The polypeptides of the invention may be administered directly, or may be administered indirectly by expression from an encoding sequence. For example, a polynucleotide may be provided that encodes a polypeptide of the invention. A polypeptide of the invention may thus be produced from or delivered in the form of a polynucleotide which encodes, and is capable of expressing, it. Any reference herein to the use, delivery or administration of a peptide of the invention is intended to include the indirect use, delivery or administration of such a peptide via expression from a polynucleotide that encodes it.

In this aspect, the invention provides a polynucleotide which encodes a polypeptide comprising, consisting or consisting essentially of the amino acid sequence of any one of SEQ ID NOs 31 to 35 or a variant derived therefrom.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide may be provided in isolated or purified form.

Polynucleotides can be synthesised according to methods well known in the art, as described by way of example in Sambrook et al (1989, Molecular Cloning—a laboratory manual; Cold Spring Harbor Press).

The above polynucleotides may be used in vitro, ex vivo or in vivo in the production of a polypeptide of the invention. Such polynucleotides may be administered or used in the prevention or treatment of allergy to *Cladosporium* and/or *Alternaria*.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

Antigen Presenting Cells (APCs)

The invention encompasses the use in vitro of a method of producing a population of APCs that present the peptides of the invention on their surface. Said population of APCs may be subsequently used in therapy. Said method of production may be carried out ex vivo on a sample of cells that have been obtained from a patient. The APCs produced in this way therefore form a pharmaceutical agent that can be used in the treatment or prevention of allergy to *Cladosporium* and/or *Alternaria*. The cells should be accepted by the immune system of the individual because they derive from that individual. Delivery of cells that have been produced in this way to the individual from whom they were originally obtained, thus forms a therapeutic embodiment of the invention.

Where an APC is to be administered, it is preferred to administer the APC to a site in the body where it will have the ability to contact, and activate, suitable T cells of the individual.

In Vitro Method

The invention further provides an in vitro method of determining whether T cells recognize a polypeptide or salt of the invention, which method comprises contacting said T cells with said polypeptide or salt and detecting whether said T cells are stimulated by said polypeptide or salt. Preferably, the method comprises use of a polypeptide, or salt thereof, comprising, consisting or consisting essentially of the amino acid sequence of any one of SEQ ID NOs 31 to 35 or a variant derived therefrom The above method may be carried out to determine whether an individual has, or is at risk of having, an allergy to *Cladosporium* and/or *Alternaria*.

The invention is illustrated by the following Examples:

EXAMPLES

Example 1

MHC Class II Binding Search

The aim of this study is to identify a distinct panel of polypeptides having sequences with strong affinities for the seven most common human MHC Class II HLA-DRB1* allotypes (covering in total around 63% of the allotypes found in the average Caucasian population). In order to identify said polypeptides in the major *Cladosporium* allergens Cla h 6, Cla h 8 and Cla h 10 from *Cladosporium herbarium* and in Cla c 9 from *Cladosporium cladosporoides*, an in silico approach known as "peptide threading" was performed using the commercially available EpiMatrix algorithm (EpiVax Inc.) This is a bioinformatic method of analysing a polypeptide having a given sequence for the potential to be accommodated within the binding groove of MHC class II HLA-DR molecules.

EpiMatrix is a matrix-based algorithm that ranks 10 amino acid long segments, overlapping by 9 amino acids, from any polypeptide sequence by estimated probability of binding to each of the selected MHC molecules. (De Groot et al., AIDS Research and Human Retroviruses 13:539-41 (1997)). The procedure for developing matrix motifs was published by Schafer et al, 16 Vaccine 1998 (1998). In this Example, binding potential for HLA DR1, DR2, DR3, DR4, DR7, DR8, DR11, DR13 and DR15 is assessed. Putative MHC ligands are selected by scoring each 10-mer frame in a polypeptide sequence. This score is derived by comparing the sequence of the 10-mer to the matrix of 10 amino acid sequences known to bind to each MHC allele. Retrospective studies have demonstrated that EpiMatrix accurately predicts published MHC ligands (Jesdale et al., in Vaccines '97 (Cold Spring Harbor Press, Cold Spring Harbor, N.Y., 1997)). Successful prediction of polypeptides which bind to multiple MHC molecules has also been confirmed.

Estimated probability of binding to a selected MHC molecule is calculated by EpiMatrix as follows. The polypeptides having a given sequence are scored by estimating the relative promotion or inhibition of binding for each amino acid, compared to known MHC binders for a given MHC allele. This information is summed across the polypeptide and a summary score (EMX score) is assigned to the entire polypeptide. After comparing the EMX score to the scores of known MHC ligands, EpiMatrix arrives at an "estimated binding probability" (abbreviated as EBP, but not strictly a probability). The EBP describes the proportion of polypeptides with EpiMatrix scores as high or higher that will bind to a given MHC molecule. EBPs range from 100% (highly likely to bind) to less than 1% (very unlikely to bind).

EpiMatrix analyses were performed on the entire sequence of the known isoform of Cla h 6 (NCBI accession no: P42040). These analyses identified core polypeptides (and their flanking sequences) derived from the above sequences which are predicted to have good MHC class-II binding. The sequences are shown below in Table 2.

In Table 2: "Residues in sequence" gives the location of the sequence within the sequence of the polypeptide that was analysed. The core sequence (middle amino acids in bold) defines the actual binding sequence that was identified during the analysis. The stabilizing flanks (N-terminal and C-terminal, not bold) were included for use with the core sequence and are typically required to aid manufacture of a polypeptide. "Number of hits" refers to the number of high predicted binding affinities for all MHC types tested within the sequence. The "EpiMatrix Cluster Score" is derived from the number of hits normalized for the length of the cluster. Cluster Score is thus the excess or shortfall in predicted aggregate MHC binding properties relative to a random polypeptide standard. A score above 10 is considered to indicate broad MHC binding properties.

TABLE 2

| INPUT SEQUENCE | RESIDUES IN SEQUENCE (Incl. FLANKS) | SEQUENCE | Hydro-phobicity | EpiMatrix HITS (Excl FLANKS) | Epi Matrix CLUSTER SCORE (Excl FLANKS) | Peptide ID NO: | SEQ ID NO: |
|---|---|---|---|---|---|---|---|
| P42040 | 187-204 | AEV**YQKLKSLTKKRY**GQS | -1.24 | 7 | 11.66 | P49 | 1 |
| P42040 | 234-254 | EAG**YTGQIKIAMDVASSE**FYK | -0.20 | 10 | 15.17 | P50 | 2 |
| P42040 | 364-385 | KDS**FAAGWGVMVSHRSGET**EDV | -0.45 | 9 | 13.37 | P51 | 3 |
| P42040 | 387-402 | IAD**IVVGLRAGQI**KTG | 0.75 | 7 | 13.05 | P52 | 4 |

Based on a further analysis of Epimatrix data, and based on homology with MHC-binding polypeptides from Alt a 6, the following additional sequences from Cla h 6 were also identified as having suitable MHC-binding properties: MAVAKAAAA (SEQ ID NO: 5), YQKLKSLTK (SEQ ID NO: 6), WGVMVSHRS (SEQ ID NO: 7), YTGQIKIAM (SEQ ID NO: 8), IKIAMDVAS (SEQ ID NO: 9).

Based on homology with Cla h 6 and further design and screening, the following sequences derived from Alt a 6 were also identified as having suitable MHC-binding properties:

SEQ ID NO: 38 (Alt13A; AEVYQKLKALAKKTYGQ), SEQ ID NO: 39 (Alt14; GWGVMVSHRSGET), SEQ ID NO: 40 (Alt14A; GWGV-Nle-VSHRSGET), SEQ ID NO: 41 (Alt15; GYTGKIKIAMDVASSE), SEQ ID NO: 42 (Alt15A; GYTGKIKIA-Nle-DVASSE). Nle: Norleucine.

Example 2

EpiMatrix analyses as above were performed on the entire sequence of the known isoform of Cla h 8 (NCBI accession no: P0C0Y5). This analysis identified core sequences (with their flanking sequences) derived from said Cla h 8 isoform which are predicted to have good MHC class-II binding properties. These sequences are shown below in Table 3. Headings and notes for Table 3 are as with Table 2 above.

(SEQ ID NO: 16), FVPKETQQL (SEQ ID NO: 17), WHSMIPMGR (SEQ ID NO: 18), LKGAYVYFA (SEQ ID NO: 19), YVYFASDAS (SEQ ID NO: 20). SEQ ID NO:s 19 and 20 are variants of SEQ ID NO: 12.

le;3qBased on homology with Cla h 8 and further design and screening, the following sequences derived from Alt a 8 were also identified as having suitable MHC-binding properties:

SEQ ID NO: 43 (Alt20; LAITYNSRAEGAEK), SEQ ID NO: 44 (Alt21; GLHFRERKTGSLVIT), SEQ ID NO: 45 (Alt23; NEWRDFARVNSISP), SEQ ID NO: 46 (Alt 24; KLWHSMIPMGRDAK), SEQ ID NO: 47 (Alt24A; KLWHS-Nle-IP-Nle-GRDAK), SEQ ID NO: 48 (Alt24B KLWHS-Nle-IPMGRDAK), SEQ ID NO: 49 (Alt 24C; KLWHSMIP-Nle-GRDAK).

Example 3

EpiMatrix analyses as above were performed on the entire sequence of known isoforms of Cla h 10 (NCBI accession

TABLE 3

| INPUT SEQUENCE | RESIDUES IN SEQUENCE (Incl. FLANKS) | SEQUENCE | Hydro-phobicity | Epi Matrix HITS (Excl FLANKS) | Epi Matrix CLUSTER SCORE (Excl FLANKS) | Peptide ID NO: | SEQ ID NO: |
|---|---|---|---|---|---|---|---|
| P0C0Y5 | 42-64 | CAE**MGAAVAITYASRAQGAE**ENV | 0.19 | 9 | 12.14 | P53 | 10 |
| P0C0Y5 | 144-168 | GHH**FKERGTGSLVITASMSGHI**ANF | -0.09 | 11 | 14.86 | P54 | 11 |
| P0C0Y5 | 150-204 | ANE**WRDFARVNS**ISP | -0.80 | 5 | 10.04 | P55 | 51 |
| P0C0Y5 | 235-256 | AKE**LKGAYVYFASDASTYT**TGA | -0.15 | 11 | 14.42 | P56 | 12 |

Based on a further analysis of Epimatrix data, and based on homology with MHC binding polypeptides from Alt a 8, the following additional sequences from Cla h 8 were also identified as having suitable MHC-binding properties: ITYASRAQG (SEQ ID NO: 13), ERGTGSLVI (SEQ ID NO: 14), YNVAKAGCI (SEQ ID NO: 15), WRDFARVNS nos: P42041.2; P40108). This analysis identified core sequences (with flanking sequences) derived from the said Cla h 10 isoform which are predicted to have good MHC class-II binding. These sequences are shown below in Table 4. Headings and notes for Table 4 are as with Table 2 above.

TABLE 4

| INPUT SEQUENCE | RESIDUES IN SEQUENCE (Incl. FLANKS) | SEQUENCE | Hydro-phobicity | EpiMatrix HITS (Excl FLANKS) | EpiMatrix CLUSTER SCORE (Excl FLANKS) | Peptide ID NO: | SEQ ID NO: |
|---|---|---|---|---|---|---|---|
| P40108 | 65-83 | RQA**FEGSWRLETPENR**GKL | -1.45 | 7 | 10.13 | P57 | 21 |
| P40108 | 143-159 | PDT**FNYVKKEPIGV**CRS | -0.65 | 7 | 12.06 | P58 | 22 |
| P40108 | 240-260 | GST**VVGRTILKAAASSNL**KKV | 0.28 | 11 | 16.69 | P59 | 23 |
| P40108 | 281-300 | AIS**WVNFGIFFNHGQCC**CAG | 0.81 | 9 | 12.74 | P60 | 24 |
| P40108 | 310-330 | YDK**FVQKFKERAQKNVVG**DPF | -1.03 | 11 | 16.8 | P61 | 25 |
| P40108 | 409-431 | EDA**IKLGNASTYGLAAAVHT**KNL | -0.01 | 10 | 15.4 | P62 | 26 |
| P40108 | 477-496 | LAN**YTQTKTVSIRLGDALFG** | 0.13 | 9 | 14.28 | P63 | 27 |

Based on a further analysis of Epimatrix data, and based on homology with Alt a 10 MHC binding peptides, the following additional sequence from Cla h 10 was also identified as having suitable MHC-binding properties: WKIGPAIAT (SEQ ID NO: 28), YTQTKTVSI (SEQ ID NO: 29).

Based on homology with Cla h 10 and further design and screening, the following sequence derived from Alt a 10 was also identified as having suitable MHC-binding properties:

SEQ ID NO: 50 (Alt28; WSWKIGPAIATGNT).

Example 4

EpiMatrix analyses as above were performed on the entire sequence of a known isoform of *Cladosporium cladosporoides* vacuolar serine protease (Cla c 9; Uniprot accession no: B0L807). This analysis identified a core sequence (with flanking sequences) derived from the said vacuolar serine protease which is predicted to have good MHC class-II binding. This sequence is shown below in Table 5. Headings and notes for Table 5 are as with Table 2 above.

TABLE 5

| INPUT SEQUENCE | RESIDUES IN SEQUENCE (Incl. FLANKS) | SEQUENCE | Hydro-phobicity | Epi Matrix HITS (Excl FLANKS) | Epi Matrix CLUSTER SCORE (Excl FLANKS) | Peptide ID NO: | SEQ ID NO: |
|---|---|---|---|---|---|---|---|
| B0L807 | 337-349 | GGY**KAAVRPTML**E | -0.215 | 11 | 15.77 | P64 | 35 |

In addition, the sequence GLFISTGTQGGGQ (SEQ ID NO: 37) derived from Cla h 7 was identified based on homology with an MHC-binding polypeptide from Alt a 7.

Example 5

The sequences set out in Table 6 were selected by the inventors as having desirable characteristics, based on the analyses performed in Examples 1 to 4 and a consideration of solubility and other physicochemical characteristics. The sequences of SEQ ID NOS: 30 and 36 are preferred variant sequences derived from SEQ ID NOS: 32 and 35, respectively. These variant sequences were selected for improved solubility and/or manufacturability relative to the original amino acid sequences. Polypeptides consisting of the sequences of Table 6 were produced and were particularly preferred for screening in subsequent assays. The polypeptide of SEQ ID NO: 30 (Cla25A) is typically used in place of the polypeptide of SEQ ID NO: 32 (Cla25) in said assays.

TABLE 6

| Peptide | Sequence | Residues in parent | SEQ ID NO. |
|---|---|---|---|
| Cla16 | AEVYQKLKSLTKK | 187-199 (Cla h 6) | 31 |
| Cla25 | VAITYASRAQGAE | 49-61 (Cla h 8) | 32 |
| Cla25A | VAITYASRAQGAEK | 49-61 + K (Cla h 8) | 30 |
| Cla26 | GHHFKERGTGSLVIT | 144-158 (Cla h 8) | 33 |
| Cla29 | ANYTQTKTVSIRL | 478-490 (Cla h 10) | 34 |

TABLE 6-continued

| Peptide | Sequence | Residues in parent | SEQ ID NO. |
|---|---|---|---|
| Cla35 | GGYKAAVRPTMLE | 337-349 (Cla c 9) | 35 |
| Cla35A | GGYKAAVRPT-Nle-LE | 337-349 | 36 |

Example 6

In Vitro Binding Analysis

Polypeptides having the sequences identified in Examples 1 to 5 are pre-screened for solubility in an aqueous, acidic milieu and the peptides are tested in an in vitro MHC Class II binding assay.

Methods

The assay employed is a competitive MHC class II binding assay, wherein each polypeptide is analysed for its ability to displace a known control binder from each of the human MHC class II allotypes investigated. The allotypes and control polypeptides used in this study are those shown below:

| Allotype | Control Polypeptide | Sequence |
|---|---|---|
| DRB1*0301 | *Myco. tuberculosis/ leprae* hsp 65 2-16 | AKTIAYDEEARRGLE (SEQ ID NO: 55) |
| DRB1*1101 | Influenza haemagglutinin 307-319 | PKYVKQNTLKLAT (SEQ ID NO: 56) |
| DRB1*1501 | Human myelin basic protein 85-99 | ENPVVHFFKNIVTPR (SEQ ID NO: 57) |

Each polypeptide is analysed in the competition assay and screened for relative binding compared to the control polypeptides. Due to the nature of the competitive assay the data for each polypeptide is determined as a ratio of its own IC50 to that of the control polypeptide. Thus, a polypeptide that has an IC50 value that is parity to the control polypeptide has an identical binding affinity, while peptides with a ratio less than one have a higher affinity and those with a ratio greater than one have a lower affinity.

Solubility in aqueous solution is an essential criterion for a polypeptide to be an effective therapeutic agent. Therefore, as a consequence of the solubility screen very hydrophobic polypeptides with a high frequency of large hydrophobic amino acid residues in multiple binding registers will be eliminated. This is a characteristic of promiscuous HLA-DRB1* binders. Polypeptides which bind to one or more of the MHC Class II allotypes are identified. It would be expected that such polypeptides would have the ability to bind similar allotypes that have not been tested through the homology of MHC structures.

Example 7

The following methods are used to evaluate T cell activation characteristics of polypeptides having the sequences identified in Examples 1 to 5.

Cell Proliferation Assay

The cell proliferation assay is performed on PBMC's ($140\times10^6$ cells required for all parameters to be tested). Proliferation is measured by the incorporation of the radiolabelled compound 3H-thymidine. In more detail, 100 μl of the appropriate antigen or polypeptide concentration is distributed into the appropriate wells of 96 well plates. The plates are then placed into a humidified 5% CO2 incubator set at 37° C. for a maximum of 4 hours. PBMC's isolated as described above are prepared to a concentration of $2\times10^6$ cells/ml in complete medium at room temperature. 100 μl of cell solution is then distributed into each of the wells of the 96 well plates containing antigen/polypeptide. The plates are then incubated for 6 to 8 days. The cultures are pulsed with tritiated thymidine solution by adding 10 μl of tritiated thymidine stock solution (1.85 MBq/ml in serum-free RPMI medium) to each well. The plates are then returned to the incubator for between 8 and 16 hours. Cultures are then harvested using a Canberra Packard FilterMate 196 cell harvester. Dried filter mats are counted using an appropriate beta scintillation counter.

Counts from wells containing polypeptide are compared statistically to wells containing media alone (12 wells per group). The non-parametric Mann-Whitney test is used. The same statistical test is used for all subjects. A statistically significant difference between media only wells and polypeptide-stimulated wells is considered a positive stimulation of PBMC's by the polypeptide.

Cytokine Release Assay

Polypeptides for use in this assay were manufactured at small scale (approximately 10 mg batch size, non-GMP). The purity of each polypeptide was at least 95% by HPLC. 96 well culture plates containing polypeptides and controls (the negative control was culture medium and the positive controls were staphylococcal enterotoxin B (SEB) 25 ng/ml and whole *Alternaria* allergen extract 100 μg/ml) were prepared in advance and stored at −20° C. prior to the day of assay. Polypeptides were added to wells in a volume of 100 μl containing polypeptides at a concentration of 200 μg/ml, such that subsequent addition of 100 μl of cells would create a final assay concentration of 100 μg/ml.

Peripheral blood mononuclear cells (PBMCs) were isolated from heparinised blood by Ficoll density gradient centrifugation. A 100 μl aliquot of a 5×106 cell/ml PBMC suspension was then added to each well and the plates placed in a humidified 5% CO2 incubator at 37° C. for 5 days. Following stimulation, culture supernatants (100 μl) were harvested for testing by multiplex bead assay.

Multiplex cytokine bead assays (IL-10, IL-13, Interferon gamma (IFN-g)) were performed on thawed culture supernatants according to the manufacturer's instructions. Single measurements were performed for each culture supernatant sample. After completion of the multiplex assay, individual cytokine levels were determined by interpolation from the standard curve generated in the assay. A positive result was taken as a cytokine release of greater than 50 pg/ml in one or more of the IL-13, IL-10 and IFN-g assays. The number of responders out of 50 mould allergic subjects tested was calculated for each polypeptide for the three cytokines.

Results for the polypeptides having the sequences of Table 6 are summarized in Table 8.

TABLE 8

| Polypeptide | % responders |
|---|---|
| Cla16 | 36 |
| Cla25A | 44 |
| Cla26 | 44 |
| Cla29 | 48 |
| Cla35 | 34 |
| Cla35A | 48 |

The number of responders out of the 50 mould allergic subjects tested showing an IFN-g release of greater than 100 pg/ml was also calculated for each polypeptide. Results for the polypeptides having the sequences of Table 6 are summarized in Table 9.

TABLE 9

| Polypeptide | % responders |
|---|---|
| Cla16 | 16 |
| Cla25A | 22 |
| Cla26 | 28 |
| Cla29 | 28 |
| Cla35 | 28 |
| Cla35A | 42 |

All five polypeptides comprising sequences derived from *Cladosporium* (the sequences of Cla16, Cla25A, Cla26, Cla29, and Cla35) showed responses in the population. The polypeptide having the sequence of Cla35A provided for an increased response compared to the polypeptide having the sequence of Cla35 and was the top-performing *Cladosporium*-derived polypeptide, also having the highest proportion of IFN-g (release >100 pg/ml) responders. A polypeptide having the sequence of Cla35 or Cla35A is preferred for treatment or prevention of *Cladosporium* allergy. Other top performing *Cladosporium*-derived polypeptides included those having the sequences of Cla26 and Cla25A. A polypeptide having either of these sequences is therefore also preferred for treatment or prevention of *Cladosporium* allergy.

A number of polypeptides having sequences derived from *Alternaria* allergens, which sequences have homology with corresponding regions of *Cladosporium* allergens, were also tested and showed responses in the population. A positive result was taken as a cytokine release of greater than 50 pg/ml in one or more of the IL-13, IL-10 and IFN-g assays. The number of responders out of 50 mould allergic subjects tested was calculated for each polypeptide for the three cytokines. Results are shown in Table 10 below.

TABLE 10

| Polypeptide | % responders |
|---|---|
| Alt13A | 86 |
| Alt14 | 44 |
| Alt14A | 56 |
| Alt15 | 56 |
| Alt15A | 42 |
| Alt20 | 38 |
| Alt21 | 38 |
| Alt23 | 40 |
| Alt24 | 34 |
| Alt24A | 40 |
| Alt24B | 30 |
| Alt24C | 36 |
| Alt28 | 52 |

As shown, the top performing *Alternaria*-derived polypeptide has the sequence of Alt13A. Other top performing *Alternaria*-derived polypeptides include those having the sequences of Alt14, Alt14A, Alt15, Alt15A and Alt28. These polypeptides induce positive responses in a high proportion of subjects and are thus advantageous in terms of population coverage. One or more of these polypeptides may be preferably included in combination with the *Cladosporium*-derived peptides described above in a polypeptide combination of the invention for the treatment or prevention of *Cladosporium* and/or *Alternaria* allergy.

Example 8

Preparation of Peptides, Salts and Pharmaceutical Formulations

Peptides are prepared as follows. Synthesis is performed in a solid phase peptide synthesis (SPPS) reactor and started by suspending the substituted resin in N,N-dimethylformamide (DMF). After washing of the resin with DMF, each coupling procedure is performed by addition of the N-α-protected amino acid derivative or the N-α-protected dipeptide to the preceding amino acid in the presence of N-[(1H-Benzotriazol-1-yl)(dimethylamino)methylene]-N-methylmethanaminium tetrafluoroborate N-oxide (TBTU) and N,N-diisopropylethylamine (DIPEA) in DMF or diisopropylcarbodiimide (DIC) and 1-hydroxybenzotriazole (HOBt) in a mixture of methylene chloride (DCM) and DMF. For each single step, the solvents and/or reagents are added and the reaction mixture is stirred and subsequently filtered to remove solvents and/or reagents from the resin.

After each successful coupling or capping procedure, an Fmoc-deprotection procedure is performed. It consists of washing of the resin with DMF, cleaving the Fmoc-group with 20% (V/V) piperidine in either DMF or 1-Methyl-2-pyrrolidone (NMP), and subsequent washings with DMF and isopropanol (IPA). For each single step, the solvents and/or reagents are added, and the reaction mixture is stirred and then filtered to remove the solvents and/or reagents from the resin.

Fmoc-deprotection and coupling procedures are repeated until the resin carries the complete peptide sequence of the required peptide. The SPPS is completed by a final Fmoc-deprotection and drying of the peptide resin under reduced pressure.

Acetate or hydrochloride salts of the specified peptides are prepared by the following methods. The peptide resin is treated with cold trifluoroacetic acid (TFA) at room temperature for 1.5 to 3 hours in the presence of 1,2-ethanedithiol (EDT), triisopropylsilane (TIS), and water. After filtering off and washing the resin with TFA, the product is precipitated in cold diisopropyl ether (IPE). It is then filtered off, washed with IPE, and dried under reduced pressure. The product is then reconstituted and purified by high-performance liquid chromatography (HPLC).

For preparation of acetate salts, the trifluoroacetate salt is reconstituted in 5% (V/V) aqueous acetic acid and loaded onto an ion exchange resin. The elution is performed with 5% (V/V) aqueous acetic acid. The acetate is filtered through a 0.2 μm membrane filter and lyophilized to yield the final product as a white to off-white powder.

For preparation of hydrochloride salts, the trifluoroacetate salt is reconstituted in 0.01 M HCl in purified water and filtered where necessary. The solution is loaded onto a preparative HPLC column for ion exchange into the hydrochloride salt. The ion exchange is performed by washing the column with a 0.1 M ammonium chloride solution followed by 0.01 M HCl. Subsequently, the hydrochloride is filtered through a 0.2 μm membrane filter and lyophilized to yield the final product as a white to off-white powders.

An exemplary pharmaceutical formulation of the present invention contains one or more, such as two, three, four or all of the polypeptides Cla35, Cla16, Cla25, Cla26 and Cla29 in salt form. The polypeptide Cla35A may be used in place of Cla35. The polypeptide Cla25A may be used in place of Cla25. The peptide salt is typically an acetate or hydrochloride salt. The peptide salt(s) are each typically present at a nominal concentration of 40 to 220 μM. The pharmaceutical formulation optionally further comprises one or more of L-methionine as an antioxidant (optionally at a nominal concentration of 1 to 15 mM, typically 5 mM); phosphoric acid, hydrochloric acid or aqueous ammonia for pH adjustment (as required); and trehalose dihydrate as a tonicity agent (optionally at a nominal concentration of 260 mM). The pharmaceutical formulation is prepared in solution prior to being subjected to freeze-drying to produce a lyophilisate.

The invention claimed is:

1. A method of treating an individual for or preventing in an individual allergy to *Cladosporium* and/or *Alternaria*, which method comprises administering to said individual a therapeutically or prophylactically effective amount of (i) a polypeptide, or a pharmaceutically acceptable salt thereof, which is up to 30 amino acids in length and comprises:

(I) the amino acid sequence:

(a) GGYKAAVRPTMLE, (SEQ ID NO: 35; Cla35)

(b) GHHFKERGTGSLVIT, (SEQ ID NO: 33; Cla26)
or (c) ANYTQTKTVSIRL; (SEQ ID NO: 34; Cla29)

or (II) a T cell epitope-containing variant sequence which is a said amino acid sequence (I) having up to three amino acid modifications, wherein the modification is a deletion, substitution or insertion; or of (ii) a pharmaceutical formulation which comprises a pharmaceutically acceptable carrier or diluent and a polypeptide of (i), or a pharmaceutically acceptable salt thereof.

2. A method according to claim 1, wherein the polypeptide comprises a said variant sequence (II) which has one or two amino acid modifications, wherein the modification is a deletion or substitution.

3. A method according to claim 1, wherein the substitution is a conservative substitution.

4. A method according to claim 1, wherein the polypeptide comprises a said variant sequence (II) which has up to two amino acids deleted from the N-terminus or up to two amino acids deleted from the C-terminus.

5. A method according to claim 1, wherein the polypeptide is up to 20 amino acids in length.

6. A method according to claim 1, wherein the polypeptide has an amino acid sequence consisting of a said sequence (I) or (II) having a N-terminal and/or C-terminal extension of from one to six amino acids corresponding respectively to the one to six amino acids immediately N-terminal or C-terminal to the said sequence (I) in the native sequence of the protein from which the said sequence (I) is derived.

7. A method according to claim 1, wherein the polypeptide has the amino acid sequence GGYKAAVRPT-Nle-LE (SEQ ID NO: 36; Cla35A).

8. A method according to claim 1, wherein the pharmaceutical formulation comprises two or more said polypeptides or salts thereof.

9. A method according to claim 1, wherein the pharmaceutical formulation further comprises at least one polypeptide, or a pharmaceutically acceptable salt thereof, which is up to 30 amino acids in length and comprises:

(III) the amino acid sequence:

(f) GWGVMVSHRSGET; (SEQ ID NO: 39; Alt14)

(g) GYTGKIKIAMDVASSE, (SEQ ID NO: 41; Alt15)
or (h) WSWKIGPAIATGNT; (SEQ ID NO: 50; Alt28)

or (IV) a T cell epitope-containing variant sequence which is a said amino acid sequence (III) having up to three amino acid modifications, wherein the modification is a deletion, substitution or insertion.

10. A method according to claim 1, wherein the pharmaceutical formulation is formulated for intradermal administration, subcutaneous administration, oral administration, nasal administration, topical administration, sublingual administration, buccal administration or epidermal administration.

11. A method according to claim 1, wherein the polypeptide or pharmaceutical formulation to be administered is provided in a sealed container, an ampoule, sealed vial, syringe, cartridge, flexible bag or a glass bottle.

12. A method according to claim 1, wherein the polypeptide is provided in an amount of 100 ng to 2 mg.

13. A method according to claim 1, wherein the polypeptide is provided at a concentration in solution in the range of 0.03 to 200 nmol/ml.

14. A method according to claim 1, wherein the polypeptide is provided at a concentration in solution in the range of 0.3 to 200 nmol/ml.

15. A method according to claim 1, wherein the polypeptide is provided at a concentration in solution in the range of 30 to 200 nmol/ml.

16. A method according to claim 1, wherein the polypeptide is provided in the form of a pharmaceutically acceptable salt thereof.

17. A method according to claim 16, wherein said pharmaceutically acceptable salt is selected from the group consisting of a mineral acid salt and an organic acid salt.

18. The method according to claim 16, wherein each said pharmaceutically acceptable salt is selected from the group consisting of hydrochloride, hydrobromide, phosphate, sulphate, acetate, propionate, malonate and benzoate.

19. The method according to claim 18, wherein the pharmaceutically acceptable salt is selected from the group consisting of hydrochloride and acetate.

20. The method according to claim 1, wherein the pharmaceutical formulation of (ii) further comprises at least one polypeptide, or a pharmaceutically acceptable salt thereof, which is up to 30 amino acids in length and comprises:

(III) the amino acid sequence:

(d) AEVYQKLKSLTKK (SEQ ID NO: 31; Cla16), or (e) VAITYASRAQGAE (SEQ ID NO: 32; Cla25); or (IV) a T cell epitope-containing sequence which is a said amino acid sequence (III) having up to three modifications, wherein the modification is a deletion, substitution or insertion.

21. The method according to claim 20, wherein the polypeptide has the amino acid sequence VAITYASRAQGAEK (SEQ ID NO: 30; Cla25A).

22. A method of treating an individual for or preventing in an individual allergy to *Cladosporium* and/or *Alternaria*, which method comprises administering to said individual a therapeutically or prophylactically effective amount of (i) a polypeptide, or a pharmaceutically acceptable salt thereof, which is up to 30 amino acids in length and comprises:

(I) the amino acid sequence GGYKAAVRPTMLE (SEQ ID NO: 35; Cla35), or (II) a T cell epitope-containing variant sequence which is a said amino acid sequence (I) having up to three amino acid modifications, wherein the modification is a deletion, substitution or insertion; or of (ii) a pharmaceutical formulation which comprises a pharmaceutically acceptable carrier or diluent and a polypeptide of (i), or a pharmaceutically acceptable salt thereof.

23. A method of treating an individual for or preventing in an individual allergy to *Cladosporium* and/or *Alternaria*, which method comprises administering to said individual a therapeutically or prophylactically effective amount of (i) a polypeptide, or a pharmaceutically acceptable salt thereof, which is up to 30 amino acids in length and comprises:

(I) the amino acid sequence

```
(a)  GGYKAAVRPTMLE,    (SEQ ID NO: 35; Cla35)

(b)  GHHFKERGTGSLVIT, (SEQ ID NO: 33; Cla26)
or

(c)  ANYTQTKTVSIRL;    (SEQ ID NO: 34; Cla29)
```

or (II) a variant sequence which is a said amino acid sequence (I) which has one or two amino acid modifications wherein the modification is a deletion or substitution; or of (ii) a pharmaceutical formulation which comprises a pharmaceutically acceptable carrier or diluent and a polypeptide of (i), or a pharmaceutically acceptable salt thereof.

24. A method according to claim 23, wherein the substitution is a conservative substitution.

25. A method according to claim 23, wherein the polypeptide comprises a said variant sequence (II) which has up to two amino acids deleted from the N-terminus and/or up to two amino acids deleted from the C-terminus.

26. A method according to claim 23, wherein the polypeptide is up to 20 amino acids in length.

27. A method according to claim 23, wherein the polypeptide has an amino acid sequence consisting of a said sequence (I) or (II) having a N-terminal and/or C-terminal extension of from one to six amino acids corresponding respectively to the one to six amino acids immediately N-terminal or C-terminal to the said sequence (I) in the native sequence of the protein from which the said sequence (I) is derived.

28. A method according to claim 20, wherein the pharmaceutical formulation comprises:

a polypeptide having the amino acid sequence (I)(a) or a said variant sequence (II) derived therefrom, or a said salt thereof;

a polypeptide having the amino acid sequence (I)(b) or a said variant sequence (II) derived therefrom, or a said salt thereof;

a polypeptide having the amino acid sequence (I)(c) or a said variant sequence (II) derived therefrom, or a said salt thereof;

a polypeptide having the amino acid sequence(III)(d) or a said variant sequence (IV) derived therefrom, or a said salt thereof; and a polypeptide having the amino acid sequence (III)(e) or a said variant sequence (IV) derived therefrom, or a said salt thereof.

* * * * *